US 6,647,345 B2

(12) United States Patent  
Bye et al.

(10) Patent No.: US 6,647,345 B2
(45) Date of Patent: Nov. 11, 2003

(54) PORTABLE HEARING-RELATED ANALYSIS SYSTEM

(75) Inventors: Gordon J. Bye, St. Cloud, MN (US); Jeffrey C. Erdahl, Randolph, MN (US); David A. Preves, Minnetonka, MN (US)

(73) Assignee: Micro Ear Technology, Inc., Plymouth, MN (US)

( * ) Notice: Subject to any disclaimer, the term of this patent is extended or adjusted under 35 U.S.C. 154(b) by 0 days.

(21) Appl. No.: 10/112,965

(22) Filed: Mar. 29, 2002

(65) Prior Publication Data

US 2002/0111745 A1 Aug. 15, 2002

Related U.S. Application Data

(63) Continuation of application No. 09/004,788, filed on Jan. 9, 1998, now Pat. No. 6,366,863.

(51) Int. Cl.[7] .......................... H04R 25/00; G06F 19/00
(52) U.S. Cl. .......................... 702/57; 381/23.1; 381/60
(58) Field of Search .......................... 702/57; 381/23.1, 381/60, 58, 312, 314, 323; 705/41

(56) References Cited

U.S. PATENT DOCUMENTS

| | | | |
|---|---|---|---|
| 4,425,481 A | 1/1984 | Mansgold et al. | 179/107 |
| 4,606,329 A | 8/1986 | Hough | 128/1 R |
| 4,617,429 A | 10/1986 | Bellafiore | 179/107 |
| 4,628,907 A | 12/1986 | Epley | 128/1.6 |
| 4,634,815 A | 1/1987 | Marquis | 387/68.4 |
| 4,652,702 A | 3/1987 | Yoshii | 381/151 |
| 4,657,106 A | 4/1987 | Hardt | 381/68.4 |
| 4,680,799 A | 7/1987 | Henneberger | 381/68.6 |
| 4,706,778 A | 11/1987 | Topholm | 181/135 |
| 4,712,245 A | 12/1987 | Lyregaard | 381/68.6 |
| 4,735,759 A | 4/1988 | Bellafiore | 264/221 |
| 4,756,312 A | 7/1988 | Epley | 128/420.5 |
| 4,763,752 A | 8/1988 | Haertl et al. | 181/130 |

(List continued on next page.)

FOREIGN PATENT DOCUMENTS

| | | |
|---|---|---|
| EP | 0537026 | 4/1993 |
| WO | WO 01/35695 A2 * | 5/2001 |

OTHER PUBLICATIONS

Internet Web Page at http://www.siemens–hearing.com/products/pprods/persprogmain.htm,(Jul. 1999).

(List continued on next page.)

Primary Examiner—Patrick Assouad
(74) Attorney, Agent, or Firm—Schwegman, Lundberg, Woessner & Kluth, P.A.

(57) ABSTRACT

An improved hearing-related analysis programming system with a host computer for providing at least one hearing aid program and having at least one personal computer memory card international association (PCMCIA) defined port in combination with a PCMCIA Card inserted in the port and arranged for interacting with the host computer for controlling hearing-related analysis or programming of a hearing aid. The host computer provides power and ground to the PCMCIA Card and provides for downloading the hearing aid programming software to the PCMCIA Card upon initialization. A microprocessor on the PCMCIA Card executes hearing-related analysis or the programming software. A hearing aid interface for adjusting voltage levels and impedance levels is adapted for coupling signals to the hearing aid being programmed. Systems for performing hearing-related analysis include a portable audiometer system on a PCMCIA Card and operable with a portable host computer to analyze hearing of a patient, and a real-ear system on a PCMCIA Card and operable with a portable host computer to analyze output from a hearing aid in a patient's ear.

16 Claims, 13 Drawing Sheets

U.S. PATENT DOCUMENTS

| | | | |
|---|---|---|---|
| 4,776,322 A | 10/1988 | Houg et al. ................... 128/1.6 |
| 4,800,982 A | 1/1989 | Carlson ....................... 181/130 |
| 4,811,402 A | 3/1989 | Ward .......................... 381/68.6 |
| 4,815,138 A | 3/1989 | Dietelm ...................... 381/69.2 |
| 4,817,609 A | 4/1989 | Perkins et al. ............ 128/420.6 |
| 4,834,211 A | 5/1989 | Bibby et al. ................. 181/135 |
| 4,867,267 A | 9/1989 | Carlson ....................... 181/130 |
| 4,869,339 A | 9/1989 | Barton ........................ 181/130 |
| 4,870,688 A | 9/1989 | Voroba et al. ................. 381/60 |
| 4,870,689 A | 9/1989 | Weiss ......................... 381/68.6 |
| 4,879,750 A | 11/1989 | Nassler ....................... 381/68.6 |
| 4,880,076 A | 11/1989 | Ahlberg et al. ............. 181/130 |
| 4,937,876 A | 6/1990 | Biermans .................... 381/68.6 |
| 4,947,432 A | 8/1990 | Topholm ..................... 381/68.2 |
| 4,953,215 A | 8/1990 | Weiss et al. .................... 381/68 |
| 4,962,537 A | 10/1990 | Basel et al. ................. 381/68.6 |
| 4,972,488 A | 11/1990 | Weiss et al. ............... 381/68.6 |
| 4,972,492 A | 11/1990 | Tanaka et al. ............... 381/187 |
| 4,975,967 A | 12/1990 | Rasmussen ................. 381/187 |
| 4,977,976 A | 12/1990 | Major ......................... 181/130 |
| 4,989,251 A | 1/1991 | Mangold ................... 381/68.2 |
| 5,002,151 A | 3/1991 | Oliveira et al. ............. 181/130 |
| 5,003,607 A | 3/1991 | Reed .......................... 381/68.4 |
| 5,003,608 A | 3/1991 | Carlson ...................... 381/68.6 |
| 5,008,943 A | 4/1991 | Arndt et al. ................ 381/68.6 |
| 5,012,520 A | 4/1991 | Steeger ......................... 381/68 |
| 5,033,090 A | 7/1991 | Weinrich .................... 381/68.4 |
| 5,046,580 A | 9/1991 | Barton ........................ 181/135 |
| 5,048,092 A | 9/1991 | Yamagishi et al. ......... 381/187 |
| 5,068,902 A | 11/1991 | Ward .......................... 381/68.6 |
| 5,083,312 A | 1/1992 | Newton et al. ............... 381/68 |
| 5,101,435 A | 3/1992 | Carlson ...................... 381/68.6 |
| 5,133,016 A | 7/1992 | Clark ......................... 381/69.2 |
| 5,142,587 A | 8/1992 | Kobayashi .................. 381/187 |
| 5,144,674 A | 9/1992 | Meyer et al. .................. 381/68 |
| 5,146,051 A | 9/1992 | Hermann .................... 181/130 |
| 5,166,659 A | 11/1992 | Navarro ..................... 381/68.6 |
| 5,185,802 A | 2/1993 | Stanton ...................... 381/68.6 |
| 5,195,139 A | 3/1993 | Gauthier ....................... 381/69 |
| 5,197,332 A * | 3/1993 | Shennib ...................... 600/559 |
| 5,201,007 A | 4/1993 | Ward et al. ................. 381/68.6 |
| 5,208,867 A | 5/1993 | Stites, III ................... 381/169 |
| 5,220,612 A | 6/1993 | Tibbetts et al. ................ 381/68 |
| 5,222,151 A | 6/1993 | Nagayoshi et al. ......... 381/187 |
| 5,226,086 A | 7/1993 | Platt ............................ 381/58 |
| 5,257,315 A | 10/1993 | Haertl et al. ............... 381/68.6 |
| 5,259,032 A | 11/1993 | Perkins et al. ................ 381/68 |
| 5,282,253 A | 1/1994 | Konomi ...................... 381/151 |
| 5,295,191 A | 3/1994 | Van Vroenhoven ........ 381/68.6 |
| 5,298,692 A | 3/1994 | Ikeda et al. .................. 181/135 |
| 5,303,305 A | 4/1994 | Raimo et al. .................. 381/68 |
| 5,319,163 A | 6/1994 | Scott .......................... 181/130 |
| 5,321,757 A | 6/1994 | Woodfill, Jr. ................. 381/68 |
| 5,327,500 A | 7/1994 | Campbell ................... 381/68.6 |
| 5,338,287 A | 8/1994 | Miller et al. .................. 600/25 |
| 5,345,509 A | 9/1994 | Hofer et al. ................ 381/68.6 |
| 5,357,576 A | 10/1994 | Arndt ......................... 381/68.6 |
| 5,363,444 A | 11/1994 | Norris ........................ 379/430 |
| 5,365,593 A | 11/1994 | Greenwood et al. .......... 381/69 |
| 5,373,555 A | 12/1994 | Norris et al. ................ 379/430 |
| 5,381,484 A | 1/1995 | Claes et al. ................. 381/68.6 |
| 5,390,254 A | 2/1995 | Adelman ...................... 381/68 |
| 5,395,168 A | 3/1995 | Leenen ....................... 381/68.6 |
| 5,402,494 A | 3/1995 | Flippe et al. .............. 381/69.2 |
| 5,420,930 A | 5/1995 | Shugart, III ............... 381/68.6 |
| 5,425,104 A | 6/1995 | Shennib ........................ 381/68 |
| 5,448,637 A | 9/1995 | Yamaguchi et al. ......... 379/430 |
| 5,487,161 A | 1/1996 | Koenck et al. | |
| 5,530,763 A | 6/1996 | Aebi et al. .................... 381/69 |
| 5,531,787 A | 7/1996 | Lesinski et al. .............. 623/10 |
| 5,535,282 A | 7/1996 | Luca .......................... 381/68.6 |
| 5,553,152 A | 9/1996 | Newton ..................... 381/68.6 |
| 5,572,594 A | 11/1996 | Devoe et al. .............. 381/68.6 |
| 5,574,654 A * | 11/1996 | Bingham et al. ......... 324/76.12 |
| 5,590,373 A * | 12/1996 | Whitley et al. ............... 710/10 |
| 5,604,812 A * | 2/1997 | Meyer ........................ 381/312 |
| 5,606,621 A | 2/1997 | Reiter et al. ................ 381/68.6 |
| 5,645,074 A | 7/1997 | Shennib et al. ............. 128/746 |
| 5,710,819 A * | 1/1998 | Tøpholm et al. ........... 381/312 |
| 5,717,771 A * | 2/1998 | Sauer et al. ................ 381/312 |
| 5,721,783 A * | 2/1998 | Anderson ................... 381/312 |
| 5,835,611 A * | 11/1998 | Kaiser et al. ............... 381/314 |
| 5,870,481 A | 2/1999 | Dymond et al. .............. 381/60 |
| 6,058,197 A * | 5/2000 | Delage ........................ 381/312 |
| 6,366,863 B1 * | 4/2002 | Bye et al. ................... 381/23.1 |
| 6,424,722 B1 * | 7/2002 | Hagen et al. ............... 381/314 |
| 6,449,662 B1 * | 9/2002 | Armitage .................... 381/314 |

OTHER PUBLICATIONS

Internet Web Page at http://pw2.netcom.com/~ed13/pcmcia.html entitled "What is PCMCIA", (Nov. 14, 1996).

Internet Web Page at http://www.microaud.com,(May 26, 1999).

Internet Web page at www.hearing–aid.com/microcard.html entitled "Microcard PCMCIA Programming Interface", date unknown.*

* cited by examiner

PORTABLE HEARING-RELATED ANALYSIS SYSTEM

This application is a Continuation of U.S. application Ser. No. 09/004,788 now U.S. Pat. No. 6,366,863 B1, filed Jan. 9, 1998, which is incorporated herein by reference. U.S. patent application Ser. No. 08/782,328, filed on Jan. 13, 1997, and U.S. patent application Ser. No. 08/896,494, filed on Jul. 18, 1997, are hereby incorporated by reference.

BACKGROUND OF THE INVENTION

1. Field of the Invention

This invention relates generally to a portable hearing analysis system for use analyzing hearing-related conditions and for programming programmable hearing aids. More particularly, it relates to a plug-in portable hearing-related analysis system utilizing a portable host computer in conjunction with a plug-in hearing-related analysis Card that operate with a well defined port.

2. Description of the Prior Art

Hearing aids have been developed to ameliorate the effects of hearing losses in individuals. Hearing deficiencies can range from deafness to hearing losses where the individual has impairment of responding to different frequencies of sound or to being able to differentiate sounds occurring simultaneously. The hearing aid in its most elementary form usually provides for auditory correction through the amplification and filtering of sound provided in the environment with the intent that the individual can hear better than without the amplification.

Prior art hearing aids offering adjustable operational parameters to optimize hearing and comfort to the user have been developed. Parameters, such as volume or tone, may easily be adjusted, and many hearing aids allow for the individual user to adjust these parameters. It is usual that an individual's hearing loss is not uniform over the entire frequency spectrum of audible sound. An individual's hearing loss may be greater at higher frequency ranges than at lower frequencies. Recognizing these differentiations in hearing loss considerations between individuals, it has become common for a hearing health professional to make measurements that will indicate the type of correction or assistance that will be the most beneficial to improve that individual's hearing capability. A variety of measurements may be taken, which can include establishing speech recognition scores, or measurement of the individual's perceptive ability for differing sound frequencies and differing sound amplitudes. The resulting score data or amplitude/frequency response can be provided in tabular form or graphically represented, such that the individual's hearing loss may be compared to what would be considered a more normal hearing response. To assist in improving the hearing of individuals, it has been found desirable to provide adjustable hearing aids wherein filtering parameters may be adjusted, and automatic gain control (AGC) parameters are adjustable.

Various systems for measuring auditory responses are known, and prior art audiometer systems characteristically are embodied in relatively large stand-alone units. Such hearing analyzing systems are referred to as audiometers, and usually provide for application of selected tones, broadband noise, and narrow-band noise variable in frequency and amplitude, respectively, to aid in determining the amount of hearing loss a person may have. To assess hearing thresholds for speech, an audiometer may also reproduce live voice or recorded speech at selectable calibrated levels. Various complex controls are used to administer varying sound conditions to determine a range of responses for the individual. These responses can be charted or graphed, and can serve as the basis for applying programming signals to programmable hearing aids. Size and complexity result in prior art audiometers being primarily useful only in facilities primarily dedicated to hearing care. Further, there is usually a requirement that hearing response parameters determined through use of prior art audiometers be manually entered into hearing aid programming devices. Portable audiometers that can be used in conjunction with a portable hearing aid programming system are not available in the prior art.

The prior art audiometers usually include a separate housing, individual controls of various sound sources, and a separate power supply operating from its power cord or power source.

With the development of micro-electronics and microprocessors, programmable hearing aids have become well-known. It is known for programmable hearing aids to have a digital control section which stores auditory parameters and which controls aspects of signal processing characteristics. Such programmable hearing aids also have a signal processing section, which may be analog or digital, and which operates under control of the control section to perform the signal processing or amplification to meet the needs of the individual.

Hearing aid programming systems have characteristically fallen into two categories: (a) programming systems that are utilized at the manufacturer's plant or distribution center, or (b) programming systems that are utilized at the point of dispensing the hearing aid.

One type of programming system for programming hearing aids are the stand-alone programmers that are self-contained and are designed to provide the designed programming capabilities. Stand-alone programmers are available commercially from various sources. It is apparent that stand-alone programmers are custom designed to provide the programming functions known at the time. Stand-alone programmers tend to be inflexible and difficult to update and modify, thereby raising the cost to stay current. Further, such stand-alone programmers are normally designed for handling a limited number of hearing aid types and lack versatility. Should there be an error in the system that provides the programming, such stand-alone systems tend to be difficult to repair or upgrade.

Another type of programming system is one in which the programmer is connected to other computing equipment, and are available commercially.

A system where multiple programming units are connected via telephone lines to a central computer is described in U.S. Pat. No. 5,226,086 to J. C. Platt. Another example of a programming system that allows interchangeable programming systems driven by a personal computer is described in U.S. Pat. No. 5,144,674 to W. Meyer et al. Other U.S. patents that suggest the use of some form of computing device coupled to an external hearing aid programming device are U.S. Pat. No. 4,425,481 to Mansgold et al.; U.S. Pat. No. 5,226,086 to Platt; U.S. Pat. No. 5,083,312 to Newton et al.; and U.S. Pat. No. 4,947,432 to Tøtholm. Programming systems that are cable-coupled or otherwise coupled to supporting computing equipment tend to be relatively expensive in that such programming equipment must have its own power supply, power cord, housing, and circuitry, thereby making the hearing aid programmer large and not as readily transportable as is desirable.

Yet another type of hearing aid programmer available in the prior art is a programmer that is designed to install into and become part of a larger computing system. Hearing aid programmers of the type that plug into larger computers are generally designed to be compatible with the expansion ports on a specific computer. Past systems have generally been designed to plug into the bus structure known as the Industry Standard Architecture (ISA) which has primarily found application in computers available from IBM. The ISA expansion bus is not available on many present-day hand-held or lap top computers. Further, plugging cards into available ISA expansion ports requires opening the computer cabinet and appropriately installing the expansion card.

When programming is applied to programmable hearing aids, it is desirable to be able to sample the effectiveness of the programming at the ear of the wearer. To this end, another hearing-related system, referred to as so-called "real-ear" systems, have been employed to sample the output of a programmed hearing aid when in place on the user. Probe microphones are utilized to pick up the output of the hearing aid located in a user's ear, and to provide an output signal that can be compared to a target insertion gain curve for the user. Normally this requires output readings to be taken and then entered manually into the programming device to compare actual responses to predicted responses. The real-ear system automatically calculates and displays the target insertion gain curve from audiometric data that is either entered manually or by computer-to-computer transfer. This interaction of a real-ear system with a programming device generally includes delay and requires manual introduction to provide input that can be used to adjust the hearing aid programming.

Some prior art real-ear systems are very complex. For example, U.S. Pat. No. 5,645,074 to Shennib et al. describes a system for providing a three-dimensional acoustic environment to evaluate unaided, simulated aided, and aided hearing function of an individual. A part of the evaluation involves an intra-canal prosthesis that is positioned in the ear canal, and incorporates a microphone probe to measure in-the-ear-canal response at a selected reference point. This system for real-ear analysis is relatively complex, is expensive, is intended for use in providing a multidimensional profile of the ear function, and is not easily transportable. It is designed to work with a personal computer system via the Industry Standard Architecture (ISA) bus interface, so it is subject to interconnection concerns described above.

The prior art does not provide a hearing-related analyzer that operates with a hand-held computer to provide an interactive hearing aid programming system. Further, the prior art systems tend to be relatively more expensive, and are not designed to allow easy modification or enhancement of the programming software, the hearing-related analysis system software, or the various controlled programming or response parameters, while maintaining simplicity of operation, portability, and interactive functionality.

SUMMARY OF THE INVENTION

A primary objective of the invention is to provide an improved portable hearing-related analysis system for use with a system programming hearing aids, that utilizes a host computer having a pair of standardized ports, with a hearing aid programming card used with one of the pair of standardized ports and a hearing-related analyzer card used with the other of the pair of standardized ports. Hearing parameters of a user read by the audiometer can be provided to the host computer to be used in setting controls for use by the hearing aid programming card to program or adjust the programming of the hearing aids of the user. The output of a programmed hearing aid can be analyzed by a real-ear hearing-related analyzer in response to applied stimuli, and used by the host computer to adjust the programming that is applied to a programmable hearing aid.

A further primary objective of the invention in providing a small, highly transportable, inexpensive, and versatile system for analyzing a user's hearing-related responses, including measuring a user's hearing loss and measuring a real-ear hearing aid output, and programming hearing aids is accomplished through the use of host computer means for providing at least one hearing aid program, where the host computer means includes a first uniformly specified expansion port for providing power circuits, data circuits, and control circuits, and a pluggable programmer card means coupled to the first port for interacting with the host computer means for controlling programming of at least one hearing aid, the programming system including coupling means for coupling the card means to at least one hearing aid to be programmed. A second uniformly specified expansion port for providing power circuits, data circuits, and control circuits and a pluggable analyzer card means coupled to the second port for analyzing hearing-related response of a user and providing hearing parameters to the host computer means for use in controlling programming.

Another primary objective of the invention is to utilize a standardized specification defining the port architecture for a host computer, wherein a hearing-related analysis system or a hearing aid programming system can utilize any host computer that incorporates the standardized port architecture. In this regard, the personal computer memory card international association (PCMCIA) specification for the port technology allows the host computer to be selected from lap top computers, notebook computers, or hand-held computers where such PCMCIA ports are available and supported. With the present invention, it is no longer needed to provide general purpose computers, either at the location of the hearing health professional, or at the factory or distribution center of the manufacturer of the hearing aids to support the hearing-related analysis system or the programming function.

Another objective of the invention is to provide a highly portable system for programming hearing aids to thereby allow ease of usage by hearing health professionals at the point of distribution of hearing aids to individuals requiring hearing aid support. To this end, the hearing-related analysis circuitry end programming circuitry are fabricated on a Card that is pluggable to a PCMCIA socket in the host computer and is operable from the power supplied by the host computer. The hearing-related analyzing circuitry can be fabricated on one or more Cards that are pluggable to associated PCMCIA sockets in the host computer and being operable from power and software provided by the host computer.

Yet another object of the invention is to provide an improved hearing aid programming system that utilizes standardized drivers within the host computer. In this aspect of the invention, the PCMCIA card means includes a card information structure (CIS) that advises the host computer of the identification and configuration requirements of the programming circuits on the card. In one embodiment, the CIS identifies the PCMCIA Card as a serial port such that standardized serial port drivers in the host computer can service the PCMCIA Card. In another embodiment, the CIS identifies the PCMCIA Card as a unique type of hearing aid programmer Card such that the host computer would utilize drivers supplied specifically for use with that Card. In another embodiment, the CIS identifies the PCMCIA Card as a hearing-related analyzer Card, thereby indicating to the host computer that such Card drivers will be utilized. Through the use of the standardized PCMCIA architecture and drivers, PCMCIA Cards for hearing aid programming and hearing-related analysis can be utilized with any host computer that is adapted to support the PCMCIA architecture.

Still another object of the invention is to provide a hearing aid programming system that can be readily programmed and in which the controlling programming software and the controlling selectable hearing parameters can be easily modified to correct errors or adjust for different conditions. In one aspect of the invention, the programming software for hearing aid programming is stored in the memory of a host computer and is available for ease of modification or debugging on the host computer. Similarly, programming software for the hearing-related analyzer is stored in the memory of the host computer and can be modified or debugged.

Another objective of the invention is to provide an improved system wherein the hearing aid programming circuitry and the hearing-related analyzer circuitry are each mounted on Cards that meet the physical design specifications provided by PCMCIA. To this end, each Card is fabricated to the specifications of either a Type I Card, a Type II Card, or a Type III Card depending upon the physical size constraints of the components utilized. The dimensions that are not part of the PCMCIA specification, for example, the length of the Card, can be adjusted to mount the necessary complement of components.

A further objective of this invention is to provide a portable hearing-related analyzer that can be readily coupled to a PCMCIA card for controlled interaction with a host computer.

Yet another object of this invention is to provide a portable hearing-related analyzer system that can operate via a PCMCIA Card slot on a host computer to measure hearing responses of a patient in an audiometer function or to measure the output of an in-lace hearing aid in a real-ear function.

In one configuration, the audiometer comprises an audiometer capable of providing selectable variable sound sources to be applied to a patient whose hearing is being tested. The audiometer is controlled and powered by an associated host computer that functions to control operation of the audiometer by downloading control functions in response to selections entered in the host computer by the hearing care professional.

In a second configuration, the audiometer comprises a real-ear system that functions to monitor hearing aid output in the ear of the patient in response to various stimulus conditions selected by the hearing care professional, and to provide response parameters that can be compared to a predicted response utilized for initial programming of the patient's hearing aid(s).

In all configurations, there can be a variety of performance levels. In one level of performance, results of the various hearing-related analyzer configurations are manually recorded, or are provided to on-line recording apparatus. Following recording, the hearing care professional makes appropriate entry in the host computer to cause the hearing aid programmer to adjust the patient's hearing aid(s) to reflect the analysis. In a more interactive level of performance, the signals resulting from the hearing-related analysis are automatically fed back to the host computer, and are used by the programming software to provide changes in the hearing aid programming. Those changes can either be automatically and interactively provided to the hearing aid programming, or can be displayed to the hearing aid professional. When so displayed, the hearing aid professional can assess the monitored parameters and make judgments as to the most effective changes or adjustments that should be selected for optimizing the patient's hearing enhancements.

These and other more detailed and specific objectives and an understanding of the invention will become apparent from a consideration of the following Detailed Description of the Preferred Embodiment in view of the Drawings.

DETAILED DESCRIPTION OF THE PREFERRED EMBODIMENT

Figure 1:
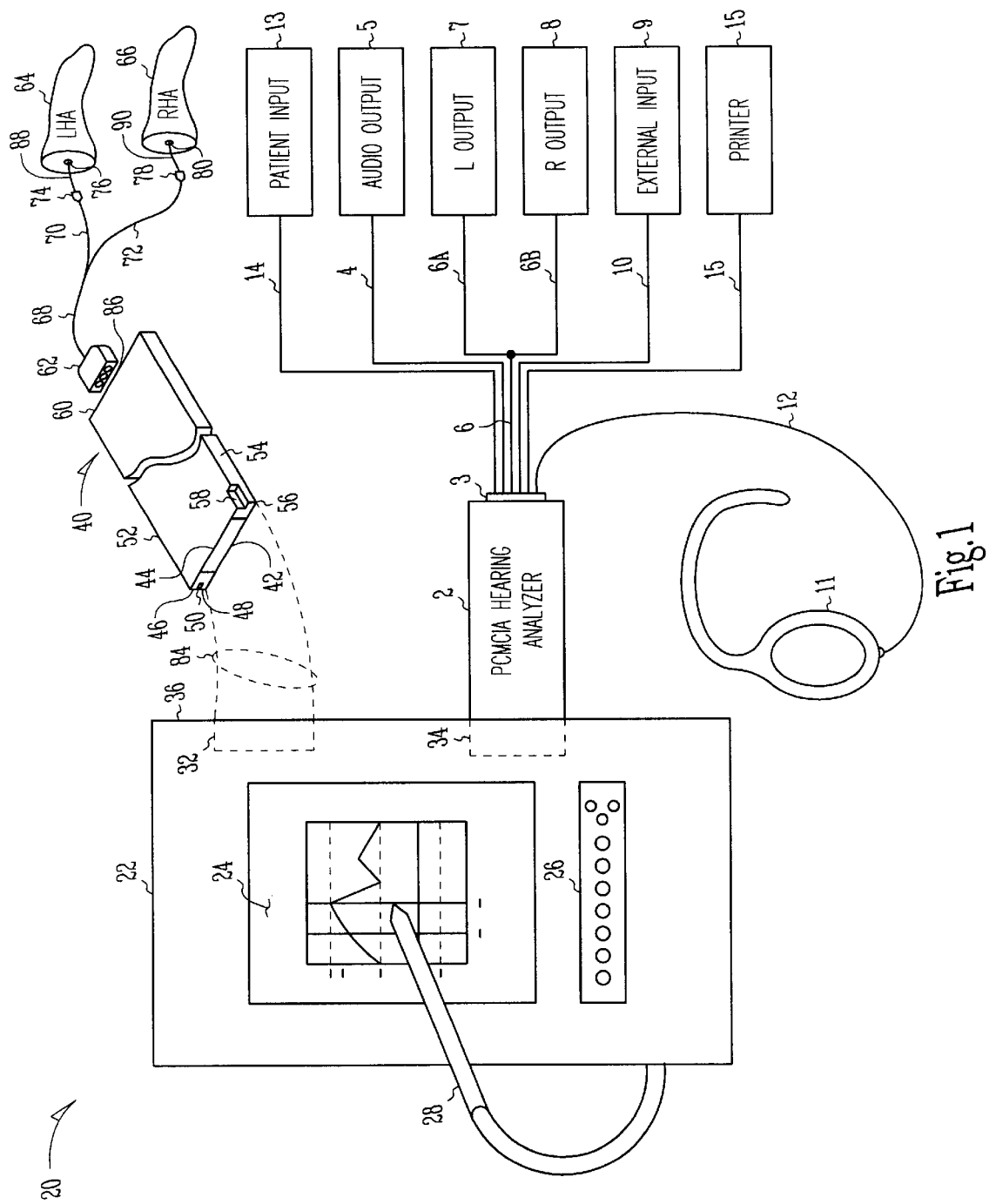
FIG. 1 is a pictorial view of an improved hearing-related analyzer and hearing aid programming system of this invention.

It is generally known that a person's hearing loss is not normally uniform over the entire frequency spectrum of hearing. For example, in typical noise-induced hearing loss, that the hearing loss is greater at higher frequencies than at lower frequencies. The degree of hearing loss at various frequencies varies with individuals. The measurement of an individual's hearing ability can be illustrated by an audiogram. An audiologist, or other hearing health professionals, will measure an individual's perceptive ability for differing sound frequencies and differing sound amplitudes. A plot of the resulting information in an amplitude/frequency diagram will graphically represent the individual's hearing ability, and will thereby represent the individual's hearing loss as compared to an established range of normal hearing for individuals. In this regard, the audiogram represents graphically the particular auditory characteristics of the individual. Other types of measurements relating to hearing deficiencies may be made. For example, speech recognition scores can be utilized. It is understood that the auditory characteristics of an individual or other measured hearing responses may be represented by data that can be represented in various tabular forms as well as in the graphical representation.

Basically a hearing aid consists of a sound actuatable microphone for converting environmental sounds into an electrical signal. The electrical signal is supplied to an amplifier for providing an amplified output signal. The amplified output signal is applied to a receiver that acts as a loudspeaker for converting the amplified electrical signal into sound that is transmitted to the individual's ear. The various kinds of hearing aids can be configured to be "completely in the canal" known as the CIC type of hearing aid. Hearing aids can also be embodied in configurations such as "in the ear", "in the canal", "behind the ear", embodied in an eyeglass frame, worn on the body, and surgically implanted. Each of the various types of hearing aids have differing functional and aesthetic characteristics. Further, hearing aids can be programmed through analog parametric adjustments or through digital programs.

Since individuals have differing hearing abilities with respect to each other, and oftentimes have differing hearing abilities between the right and left ears, it is normal to have some form of adjustment to compensate for the characteristics of the hearing of the individual. It has been known to provide an adjustable filter for use in conjunction with the amplifier for modifying the amplifying characteristics of the hearing aid. Various forms of physical adjustment for adjusting variable resistors or capacitors have been used. With the advent of microcircuitry, the ability to program hearing aids has become well-known. A programmable hearing aid typically has a digital control section and a signal processing section. The digital control section is adapted to store an auditory parameter, or a set of auditory parameters, which will control an aspect or set of aspects of the amplifying characteristics, or other characteristics, of the hearing aid. The signal processing section of the hearing aid then will operate in response to the control section to perform the actual signal processing, or amplification, it being understood that the signal processing may be digital or analog.

Numerous types of programmable hearing aids are known. As such, details of the specifics of programming functions will not be described in detail. To accomplish the programming, it has been known to have various types of programming systems that are complex, expensive, specialized in functionality, and not portable. Examples have been cited above, and specific examples are discussed in the cross-referenced patent applications. Such prior are programming systems will not be described in detail. To program hearing aids, it is generally necessary for the hearing professional to enter the audiogram or other patient-related hearing information into a computer. If properly programmed, this allows the computer to calculate the auditory parameters that will be optimal for the predetermined listening situations for the individual. The computer can then participate in the programming of the hearing aid in various ways. Prior art systems that use specific programming systems and hard-wired interrelationship to the host computer are costly and do not lend themselves to ease of altering the programming functions, and suffer from many of the problems of cost, lack of ease of usage, lack of flexibility in reprogramming, and the like.

As noted above, it is necessary to determine various hearing parameters for each patient, and to enter these audiogram parameters into the host computer. Prior art systems use separate, free-standing, expensive, and not very portable audiometers to provide controlled sound signals to analyze the patient's hearing responses. Similarly, prior art real-ear systems use separate, free-standing, expensive, and not very portable analyzers to evaluate hearing aid performance in a patient's ear(s).

The system and method of analyzing hearing responses and hearing aid performance, and programming hearing aids of the present invention provides a mechanism where all of the hearing analysis and hearing aid programming system can be economically located at the office of each hearing health professional, thereby overcoming many of the described deficiencies of prior art programming systems.

A group of commercially available computing devices, including lap top computers, notebook computers, hand-held computers, such as the Message Pad 2000, and the like, which can collectively be referenced as host computers, are adapted to support the Personal Computer Memory Card International Association Technology, and which is generally referred to as PCMCIA. In general, PCMCIA provides one or more standardized ports in the host computer where such ports are arranged to cooperate with associated PCMCIA PC Cards, hereinafter referred to as "Cards". The Cards are utilized to provide various functions, and the functionality of PCMCIA will be described in more detail below. The PCMCIA specification defines a standard for integrated circuit Cards to be used to promote interchangeability among a variety of computer and electronic products. Attention is given to low cost, ruggedness, low power consumption, light weight, and portability of operation.

The specific size of the various configurations of Cards will be described in more detail below, but in general, it is understood that it will be comparable in size to credit cards, thereby achieving the goal of ease of handling. Other goals of PCMCIA technology can be simply stated to require that (1) it must be simple to configure, and support multiple peripheral devices; (2) it must be hardware and operating environment independent; (3) installation must be flexible; and (4) it must be inexpensive to support the various peripheral devices. These goals and objectives of PCMCIA specification requirements and available technology are consistent with the goals of this invention of providing an improved highly portable, inexpensive, adaptable hearing-related analysis and hearing aid programming system. The PCMCIA technology is expanding into personal computers and work stations, and it is understood that where such capability is present, the attributes of this invention are applicable. Various aspects of PCMCIA will be described below at points to render the description meaningful to the invention.

FIG. 1 is a pictorial view of an improved hearing-related analyzer and hearing aid programming system of this invention. This illustrates the interaction of a hearing-related analyzer that can perform audiometer functions and real-ear analysis in conjunction with a host computer and a hearing aid programming system. A PCMCIA audiometer 2 has input and output signals provided through jack 3. An audiometer function is performed by the PCMCIA audiometer 2 providing selected audio signals on line 4 to audio output 5.

As will be described below, for audiometer output, audio output 5 can be a set of soundfield speakers. Further, for audiometer operation, the audio output can also be a bone vibrator. For those audiometer functions where it is desired to apply selected controlled audio signals more directly to the individual patient's ears, signals are provided on line 6 and on line 6A for the left ear illustrated as the L output 7. Similarly, the signals for the right ear are provided on line 6B to the R output 8. For signals applied directly to the patient's ears, as will be described in more detail below, the L output and R output can be air conduction headphones, or can be focused soundfield speakers.

The PCMCIA audiometer 2 normally provides the selected audio signals, but external signals can be applied from the external input 9 via line 10 into jack 3. These external input signals can be a prerecorded voice, selected signals, music, or the like, and will be selected by the hearing care professional for analysis of specific response conditions.

The hearing care professional can monitor the various selected sound signals to be applied to the patient through use of a headset 11 that is coupled via line 12 to jack 3.

A real-ear hearing-related analyzer involves the use of a probe microphone, as will be described in more detail below, inserted in the ear of the patient along with the patient's hearing aid. The real-ear system provides controlled audio output signals on line 4 to the audio output 5 and the patient's hearing aid responds to the sound stimuli as programmed. The probe microphone provides an electroacoustic measurement input 13 on line 14 to jack 3. In this manner, the real-ear analyzer can compare the measured response at the patient's hearing aid to the predicted response. The real-ear output signal is compared to a target insertion gain curve. The real-ear system calculates the target insertion gain curve from audiometric data in the system. Such data can be manually entered or entered through computer transfer. This response from the patient can be used in adjusting the programming parameters for the hearing aid programming system, thereby providing interactive programming or fine-tuning of the hearing aid(s).

The input provided from the real-ear system can also be recorded by a recording device such as printer 15 which is coupled via line 16 to the jack 3. In this manner, there is a record of the input and response for the real-ear analysis of the patient's hearing aid performance. As indicated, the various configurations of the PCMCIA audiometer Card 2 will be described in conjunction with its interrelationship to host computer 20.

Various types of host computers 20 are available commercially from various manufacturers, including, but not limited to, International Business Machines and Apple Computer, Inc. A particularly advantageous type of host computer is the hand-held computer 20 such as the Message Pad 2000, or equivalent available from commercially. The hand-held host 20 includes a body portion 22, a screen portion 24, a set of controls 26 and a stylus 28. The stylus 28 operates as a means for providing information to the hand-held host computer 20 by interaction with screen 24. A pair of PCMCIA ports 32 and 34 are illustrated aligned along one side 36 of the hand-held host computer 20. While two PCMCIA ports are shown, it should be understood that more PCMCIA ports may be utilized, usually in pairs. Further, it will be understood that it is possible for the PCMCIA ports to be position in parallel and adjacent to one another as distinguished from the linear position illustrated. The PCMCIA ports 32 and 34 each operate pursuant to the PCMCIA standard, and any description of PCMCIA functionality of one port applies to the other.

A PCMCIA Card 40 has a first end 42 in which a number of contacts 44 are mounted. In the standard, the contacts 44 are arranged in two parallel rows and number sixty-eight contacts. The outer end 60 has a connector (not shown in this figure) to cooperate with mating connector 62. This interconnection provide signals to and from hearing aids 64 and 66 via cable 68 which splits into cable ends 70 and 72.

Cable portion 70 has connector 74 affixed thereto and adapted for cooperation with jack 76 in hearing aid 64. Similarly, cable 72 has connector 78 that is adapted for cooperation with jack 80 in hearing aid 66. This configuration allows for programming of hearing aid 64 and 66 in the ears of the individual to use them, it being understood that the cable interconnection may alternatively be a single cable for a single hearing aid or two separate cables with two separations to the Card 40. The communication of hearing aid programs can alternate by way of wireless transmission 70A, which can be selected from infrared, radio frequency transmission systems. It is necessary only to adjust the type of transmitter to the receiver type in the hearing aids to be programmed.

It is apparent that Card 40 and the various components are not shown in scale with one another, and that the dashed lines represent directions of interconnection. To install the hearing aid programming system, Card 40 is moved in the direction of dashed lines 84 for insertion in PCMCIA slot 32 in host 20. Connector 62 can be moved along dashed line 86 for mating with the connector 70A at end 60 of card 40. Connector 74 can be moved along line 88 for contacting jack 76, and connector 78 can be moved along dashed line 90 for contacting jack 80. There are three standardized configurations of Card 40, plus nonstandard forms that will be described further below.

PCMCIA audiometer Card 2 is inserted in PCMCIA slot 34, and interacts with control, analyzer software, and PCMCIA requirements of host 20.

Figure 2:
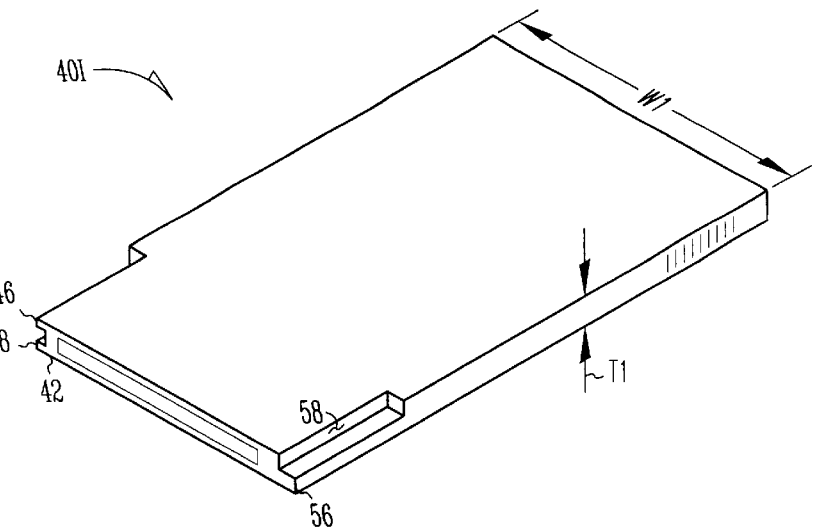
FIG. 2 is a perspective view of a Type I plug-in Card.

FIG. 2 is a perspective view of a Type I plug-in Card. The physical configurations and requirements of the various Card types are specified in the PCMCIA specification to assure portability and consistency of operation. Type I Card 40I has a width W1 of 54 millimeters and a thickness T1 of 3.3 millimeters. Other elements illustrated bear the same reference numerals as in FIG. 1.

Figure 3:
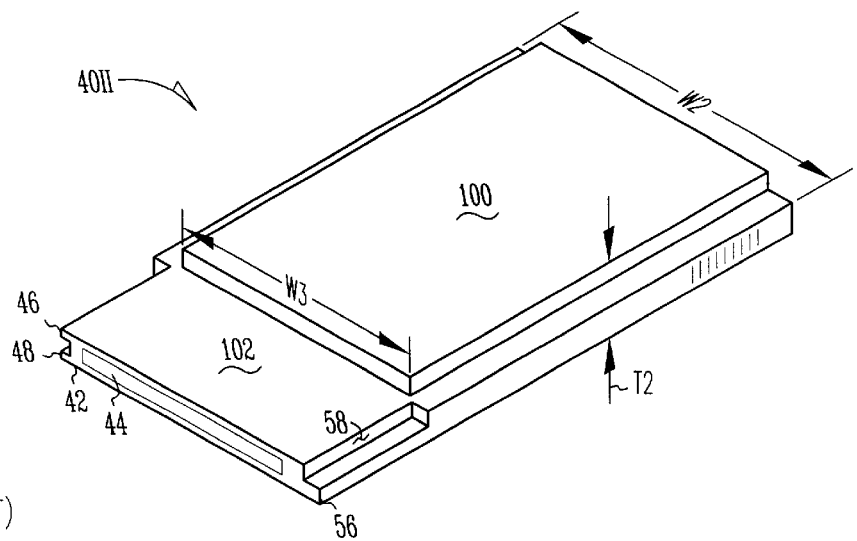
FIG. 3 is a perspective view of a Type II plug-in Card.

FIG. 3 is a perspective view of a Type II plug-in Card. Card 40II has a width W2 of 54 millimeters and has a raised portion 100. With the raised portion, the thickness T2 is 5.0 millimeters. The width W3 of raised portion 100 is 48 millimeters. The purpose of raised portion 100 is to provide room for circuitry to be mounted on the surface 102 of card 40II.

Figure 4:
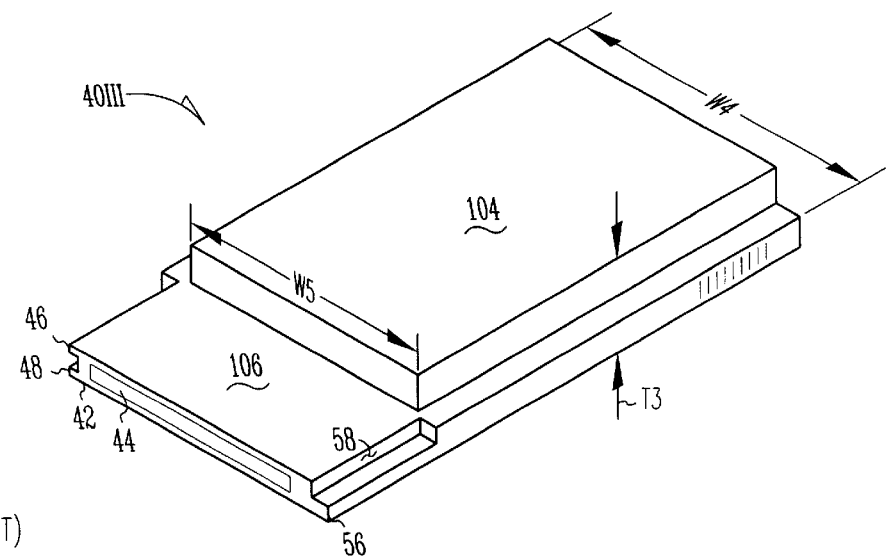
FIG. 4 is a perspective view of a Type III plug-in Card.

FIG. 4 is a perspective view of a Type III plug-in Card. Card 40III has a width W4 of 54 millimeters, and an overall thickness T3 of 10.5 millimeters. Raised portion 104 has a width W5 of 51 millimeters, and with the additional depth above the upper surface 106 allows for even larger components to be mounted.

Type II Cards are the most prevalent in usage, and allow for the most flexibility in use in pairs with stacked PCMCIA ports.

The PCMCIA slot includes two rows of 34 pins each. The connector on the Card is adapted to cooperate with these pins. There are three groupings of pins that vary in length. This results in a sequence of operation as the Card is inserted into the slot. The longest pins make contact first, the intermediate length pins make contact second, and the shortest pins make contact last. The sequencing of pin lengths allow the host system to properly sequence application of power and ground to the Card. It is not necessary for an understanding of the invention to consider the sequencing in detail, it being automatically handled as the Card is inserted. Functionally, the shortest pins are the card detect pins and are responsible for routing signals that inform software running on the host of the insertion or removal of a Card. The shortest pins result in this operation occurring last, and functions only after the Card has been fully inserted. It is not necessary for an understanding of the invention that each pin and its function be considered in detail, it being understood that power and ground is provided from the host to the Card.

Figure 5:
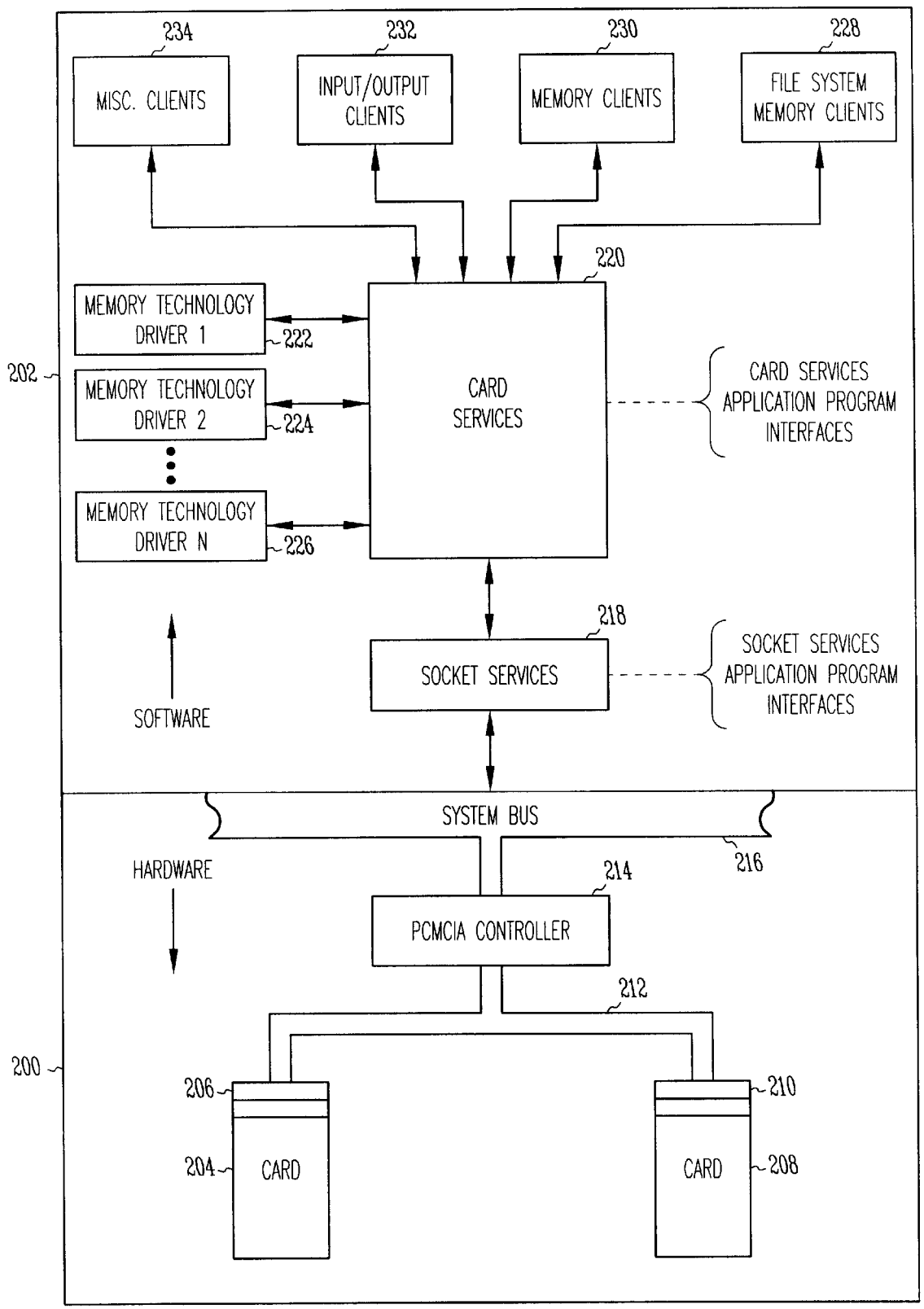
FIG. 5 is a diagram representing the PCMCIA architecture.

FIG. 5 is a diagram representing the PCMCIA architecture. The PCMCIA architecture is well-defined and is substantially available on any host computer that is adapted to support the PCMCIA architecture. For purposes of understanding the invention, it is not necessary that the intricate details of the PCMCIA architecture be defined herein, since they are substantially available in the commercial marketplace. It is, however, desirable to understand some basic fundamentals of the PCMCIA architecture in order to appreciate the operation of the invention.

In general terms, the PCMCIA architecture defines various interfaces and services that allow application software to configure Card resources into the system for use by system-level utilities and applications. The PCMCIA hardware and related PCMCIA handlers within the system function as enabling technologies for the Card.

Resources that are capable of being configured or mapped from the PCMCIA bus to the system bus are memory configurations, input/output (I/O) ranges and Interrupt Request Lines (IRQs). Details concerning the PCMCIA architecture can be derived from the specification available from PCMCIA Committee, as well as various vendors that supply PCMCIA components or software commercially.

The PCMCIA architecture involves a consideration of hardware 200 and layers of software 202. Within the hardware consideration, Card 204 is coupled to PCMCIA socket 206 and Card 208 is coupled to PCMCIA socket 210. Sockets 206 and 210 are coupled to the PCMCIA bus 212 which in turn is coupled to the PCMCIA controller 214. Controllers are provided commercially by a number of vendors. The controller 214 is programmed to carry out the functions of the PCMCIA architecture, and responds to internal and external stimuli. Controller 214 is coupled to the system bus 216. The system bus 216 is a set of electrical paths within a host computer over which control signals, address signals, and data signals are transmitted. The control signals are the basis for the protocol established to place data signals on the bus and to read data signals from the bus. The address lines are controlled by various devices that are connected to the bus and are utilized to refer to particular memory locations or I/O locations. The data lines are used to pass actual data signals between devices.

The PCMCIA bus 212 utilizes 26 address lines and 16 data lines.

Within the software 202 consideration, there are levels of software abstractions. The Socket Services 218 is the first level in the software architecture and is responsible for software abstraction of the PCMCIA sockets 206 and 210. In general, Socket Services 218 will be applicable to a particular controller 214. In general, Socket Services 218 uses a register set (not shown) to pass arguments and return status.

When interrupts are processed with proper register settings, Socket Services gains control and attempts to perform functions specified at the Application Program Interfaces (API).

Card Services 220 is the next level of abstraction defined by PCMCIA and provides for PCMCIA system initialization, central resource management for PCMCIA, and APIs for Card configuration and client management. Card Services is event-driven and notifies clients of hardware events and responds to client requests. Card Services 220 is also the manager of resources available to PCMCIA clients and is responsible for managing data and assignment of resources to a Card. Card Services assigns particular resources to Cards on the condition that the Card Information Structure (CIS) indicates that they are supported. Once resources are configured to a Card, the Card can be accessed as if it were a device in the system. Card Services has an array of Application Program Interfaces to provide the various required functions.

Memory Technology Driver 1 (MTD) 222, Memory Technology Driver 2, labeled 224, and Memory Technology Driver N, labeled 226, are handlers directly responsible for reading and writing of specific memory technology memory Cards. These include standard drivers and specially designed drivers if required.

Card Services 220 has a variety of clients such as File System Memory clients 228 that deal with file system aware structures; Memory Clients 230; Input/Output Clients 232; and Miscellaneous Clients 234.

Figure 6:
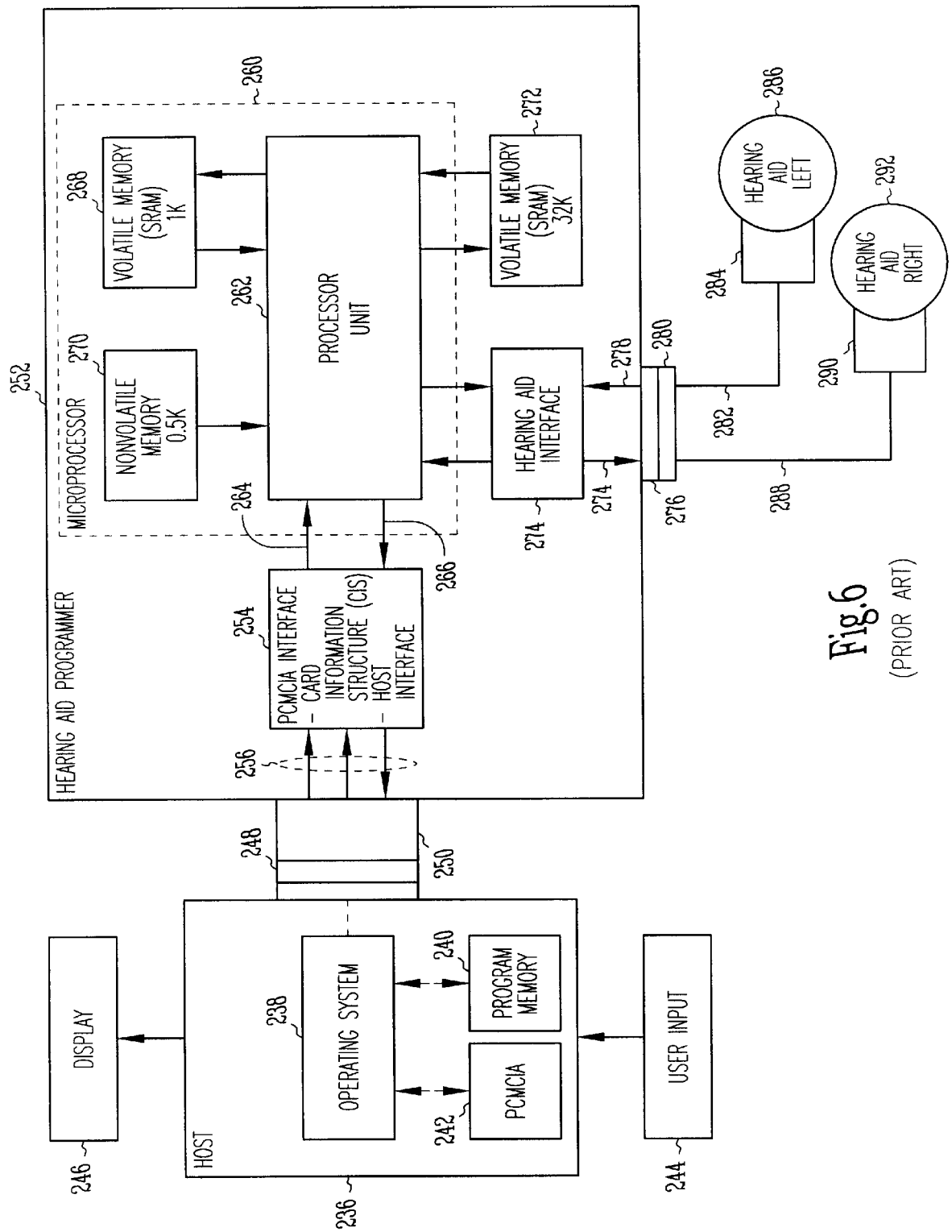
FIG. 6 is a block diagram illustrating the functional interrelationship of a host computer and the Card used for programming hearing aids.

FIG. 6 is a block diagram illustrating the functional interrelationship of a host computer and a Card used for programming hearing aids. A Host 236 has an Operating System 238. A Program Memory 240 is available for storing the hearing aid programming software. The PCMCIA block 242 indicates that the Host 236 supports the PCMCIA architecture. A User Input 244 provides input control to Host 236 for selecting hearing aid programming functions and providing data input to Host 236. A Display 246 provides output representations for visual observation. In the handheld host, the user input 244 and the display 246 are interactive, and function as the user interface. PCMCIA socket 248 cooperates with PCMCIA jack 250 mounted on Card 252.

On Card 252 there is a PCMCIA Interface 254 that is coupled to jack 250 via lines 256, where lines 256 include circuits for providing power and ground connections from Host 236, and circuits for providing address signals, data signals, and control signals. The PCMCIA Interface 254 includes the Card Information Structure (CIS) that is utilized for providing signals to Host 236 indicative of the nature of the Card and setting configuration parameters. The CIS contains information and data specific to the Card, and the components of information in CIS is comprised of tuples, where each tuple is a segment of data structure that describes a specific aspect or configuration relative to the Card. It is this information that will determine whether the Card is to be treated as a standard serial data port, a standard memory card, a unique programming card or the like. The combination of tuples is a metaformat.

A microprocessor shown within dashed black 260 includes a Processor Unit 262 that receives signals from PCMCIA Interface 254 over lines 264 and provides signals to the Interface over lines 266. An onboard memory system 268 is provided for use in storing program instructions. In the embodiment of the circuit, the Memory 268 is a volatile static random access memory (SRAM) unit of 1K capacity.

A Nonvolatile Memory 270 is provided. The Nonvolatile Memory is 0.5K and is utilized to store initialization instructions that are activated upon insertion of Card 352 into socket 348. This initialization software is often referred to as "boot-strap"software in that the system is capable of pulling itself up into operation. These memory types and sizes are illustrative and can be selected from other commercially available memory types.

A second Memory System 272 is provided. This Memory is coupled to Processor Unit 262 for storage of hearing aid programming software during the hearing aid programming operation. In a preferred embodiment, Memory 272 is a volatile SRAM having a 32K capacity. During the initialization phases, the programming software will be transmitted from the Program Memory 240 of Host 236 and downloaded through the PCMCIA interface 254. In an alternative embodiment, Memory System 272 can be a nonvolatile memory with the hearing aid programming software stored therein. Such nonvolatile memory can be selected from available memory systems such as Read Only Memory (ROM), Programmable Read Only Memory (PROM), Erasable Programmable Read Only Memory (EPROM), or Electrically Erasable Programmable Read Only Memory (EEPROM). It is, of course, understood that Static Random Access Memory (SRAM) memory systems normally do not hold or retain data stored therein when power is removed.

A Hearing Aid Interface 274 provides the selected signals over lines 274 to the interface connector 276. The Interface receives signals on lines 278 from the interface connector. In general, the Hearing Aid Interface 274 functions under control of the Processor Unit 262 to select which hearing aid will be programmed, and to provide the digital to analog selections, and to provide the programmed impedance levels.

A jack 280 couples with connector 276 and provides electrical connection over lines 282 to jack 284 that couples to hearing aid 286. In a similar manner, conductors 288 coupled to jack 290 for making electrical interconnection with hearing aid 292.

Assuming that Socket Services 218, Card Services 220 and appropriate drivers and handlers are appropriately loaded in the Host 236, the hearing aid programming system is initialized by insertion of Card 252 into socket 248. The insertion processing involves application of power signals first since they are connected with the longest pins. The next longest pins cause the data, address and various control signals to be made. Finally, when the card detect pin is connected, there is a Card status change interrupt. Once stabilized, Card Services queries the status of the PCMCIA slot through the Socket Services, and if the state has changed, further processing continues. At this juncture, Card Services notifies the I/O clients which in turn issues direction to Card Services to read the Card's CIS. The CIS tuples are transmitted to Card Services and a determination is made as to the identification of the Card 252 and the configurations specified. Depending upon the combination of tuples, that is, the metaformat, the Card 252 will be identified to the Host 236 as a particular structure. In a preferred embodiment, Card 252 is identified as a serial memory port, thereby allowing Host 236 to treat with data transmissions to and from Card 252 on that basis. It is, of course, understood that Card 252 could be configured as a serial data Card, a Memory Card or a unique programming Card thereby altering the control and communication between Host 236 and Card 252.

Figure 7:
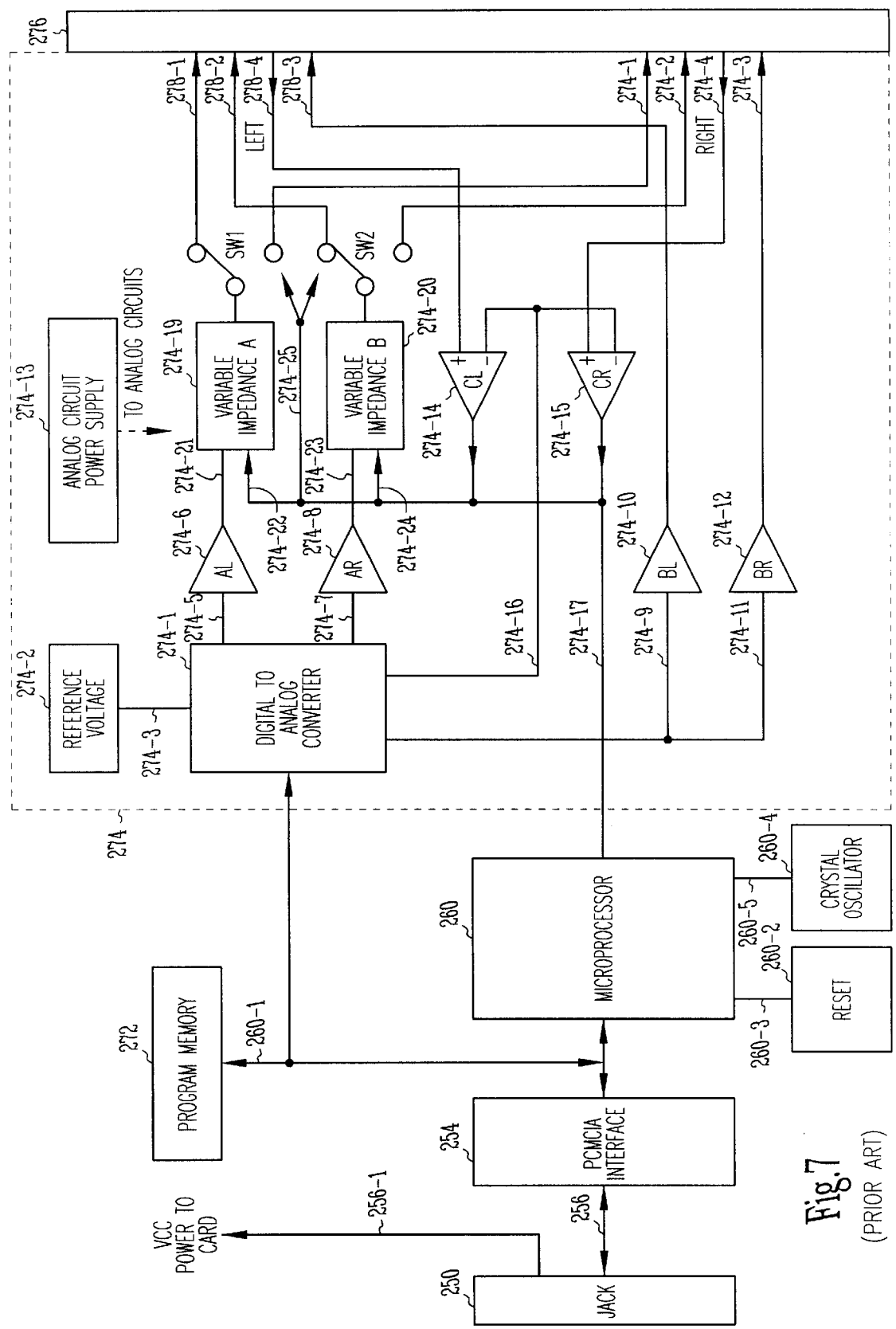
FIG. 7 is a functional block diagram of the hearing aid programming Card.

FIG. 7 is a functional block diagram of the hearing aid programming Card.

The PCMCIA jack 250 is coupled to PCMCIA Interface 254 via PCMCIA bus 256, and provides VCC power to the card via line 256-1. The Microprocessor 260 is coupled to the Program Memory 272 via the Microprocessor Bus 260-1. A Reset Circuit 260-2 is coupled via line 260-3 to Microprocessor 260 and functions to reset the Microprocessor when power falls below predetermined limits. A Crystal Oscillator 260-4 is coupled to Microprocessor 260 via line 260-5 and provides a predetermined operational frequency signal for use by Microprocessor 260.

The Hearing Aid Interface shown enclosed in dashed block 274 includes a Digital to Analog Converter 274-1 that is coupled to a Reference Voltage 274-2 via line 274-3. In a preferred embodiment, the Reference Voltage is established at 2.5 volts DC. Digital to Analog Converter 274-1 is coupled to Microprocessor Bus 260-1. The Digital to Analog Converter functions to produce four analog voltages under control of the programming established by the Microprocessor.

One of the four analog voltages is provided on Line 274-5 to amplifier AL, labeled 274-6, which functions to convert 0 to reference voltage levels to 0 to 15 volt level signals. A second voltage is provided on line 274-7 to amplifier AR, labeled 274-8, which provides a similar conversion of 0 volts to the reference voltage signals to 0 volts to 15 volt signals. A third voltage is provided on line 274-9 to the amplifier BL, labeled 274-10, and on line 274-11 to amplifier BR, labeled 274-12. Amplifiers BL and BR convert 0 volt signals to reference voltage signals to 0 volts to 15 volt signals and are used to supply power to the hearing aid being adjusted. In this regard, amplifier BL provides the voltage signals on line 278-3 to the Left hearing aid, and amplifier BR provides the selected voltage level signals on line 274-3 to the Right hearing aid.

An Analog Circuit Power Supply 274-13 provides predetermined power voltage levels to all analog circuits.

A pair of input Comparators CL labeled 274-14 and CR labeled 274-15 are provided to receive output signals from the respective hearing aids. Comparator CL receives input signals from the Left hearing aid via line 278-4 and Comparator CR receives input signals from the Right hearing aid via line 274-4. The fourth analog voltage from Digital to Analog Converter 274-1 is provided on line 274-16 to Comparators CL and CR.

A plurality of hearing aid programming circuit control lines pass from Microprocessor 260 and to the Microprocessor via lines 274-17. The output signals provided by comparators CL and CR advise Microprocessor 260 of parameters concerning the CL and CR hearing aids respectively.

A Variable Impedance A circuit and Variable Impedance B circuit 274-20 each include a predetermined number of analog switches and a like number of resistance elements. In a preferred embodiment, each of these circuits includes eight analog switches and eight resistors. The output from amplifier AL is provided to Variable Impedance A via line 274-21 and selection signals are provided via line 274-22. The combination of the voltage signal applied and the selection signals results in an output being provided to switch SWI to provide the selected voltage level. In a similar manner, the output from Amplifier R is provided on line 274-23 to Variable Impedance B 274-20, and with control signals on line 274-24, results in the selected voltage signals being applied to switch SW2.

Switches SW1 and SW2 are analog switches and are essentially single pole double throw switches that are switched under control of signals provided on line 274-25. When the selection is to program the left hearing aid, switch SWI will be in the position shown and the output signals from Variable Impedance A will be provided on line 278-1 to LF hearing aid. At the same time, the output from Variable Impedance B 274-20 will be provided through switch SW2 to line 278-2. When it is determined that the Right hearing aid is to be programmed, the control signals on line 274-25 will cause switches SW1 and SW2 to switch. This will result in the signal from Variable Impedance A to be provided on line 274-1, and the output from Variable Impedance B to be provided on line 274-2 to the Right hearing aid.

With the circuit elements shown, the program that resides in Program Memory 272 in conjunction with the control of Microprocessor 260 will result in application of data and control signals that will read information from Left and Right hearing aids, and will cause generation of the selection of application and the determination of levels of analog voltage signals that will be applied selectively the Left and Right hearing aids.

In another embodiment of the invention, a Portable Multiprogram Unit (PMU) (not shown) is adapted to store one or more hearing aid adjusting programs for a patient or user to easily adjust or program hearing aid parameters. The programs reflect adjustments to hearing aid parameters for various ambient hearing conditions. Once the PMU is programmed with the downloaded hearing aid programs, the PMU utilizes a wireless transmission to the user's hearing aid permitting the selective downloading of a selected one of the hearing aid programs to the digitally programmable hearing aids of a user.

Figure 8:
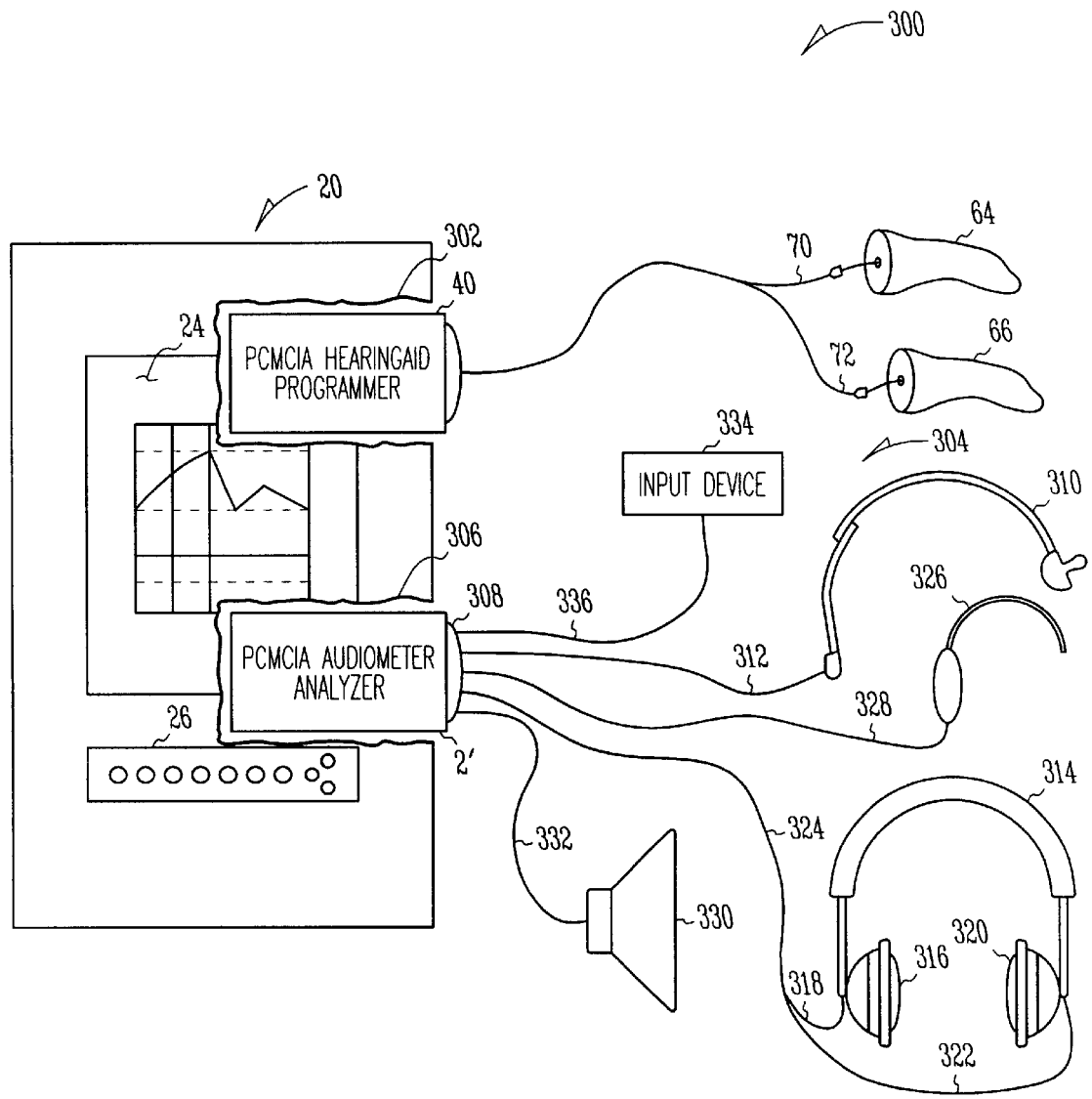
FIG. 8 is a block diagram illustrating the functional relationship of the host computer, the Card used to program hearing aids, and an audiometer Card used to analyze a patient's hearing responses.

FIG. 8 is a block diagram illustrating the functional relationship of the host computer, the Card used to program hearing aids, and the audiometer Card used to analyze a patient's hearing responses. The host computer 20 has a display 24 upon which various hearing response waveforms can be programmed for display. A hearing aid programmer system referenced generally as 300 includes the PCMCIA hearing aid programmer 40, shown within broken away portion 302 of the host 20. The PCMCIA Card 40 has cable connections 70 and 72 to hearing aids 64 and 66, respectively, as described above. An audiometer referenced generally as 304 includes a PCMCIA audiometer Card 2', shown installed within broken away portion 306 of the host 20. Connector 308 couples a bone conductor headset 310 via line 312 to the PCMCIA Card 306. A set of air conduction head phones 314 has a left speaker 316 coupled to line 318, and a speaker 320 coupled to line 322. Lines 318 and 322 are coupled via conductor 324 to connector 308 and then to the PCMCIA Card 2. An operator monitor 326 is coupled via line 328 to connector 308. A speaker 330 is coupled via line 332 to connector 308.

As will be described in more detail below, the analyzer 2 comprising an audiometer operates under control of the host processor 20 to generate selected tones, narrow band, and speech broad band acoustic signals that are transmitted to a patient whose hearing is being evaluated. The transmission to the patient is selectively accomplished through the bone conductor 310, the air conduction headphones 314, or the speaker system 330 which can comprise one or more speakers arranged in a selectable configuration to adequately test the hearing response of the patient. At the same time, the hearing aid professional can monitor the selected output signals to the patient via the monitor headset 326.

As responses are noted, the various hearing parameter responses are recorded for entry in the host computer 20.

Once the full range of hearing responses is developed, the hearing aid programmer PCMCIA Card 40 can be initiated to result in programming of hearing aids 64 and 66, in the manner described above. In an alternative configuration, the patient response can be automatically entered via input device 334 along line 336 to the audiometer. In this alternative arrangement, the response parameters are automatically passed from the audiometer to the host 20 for use in determining the hearing aid programming parameters to be utilized by the hearing aid programmer 40.

Figure 9:
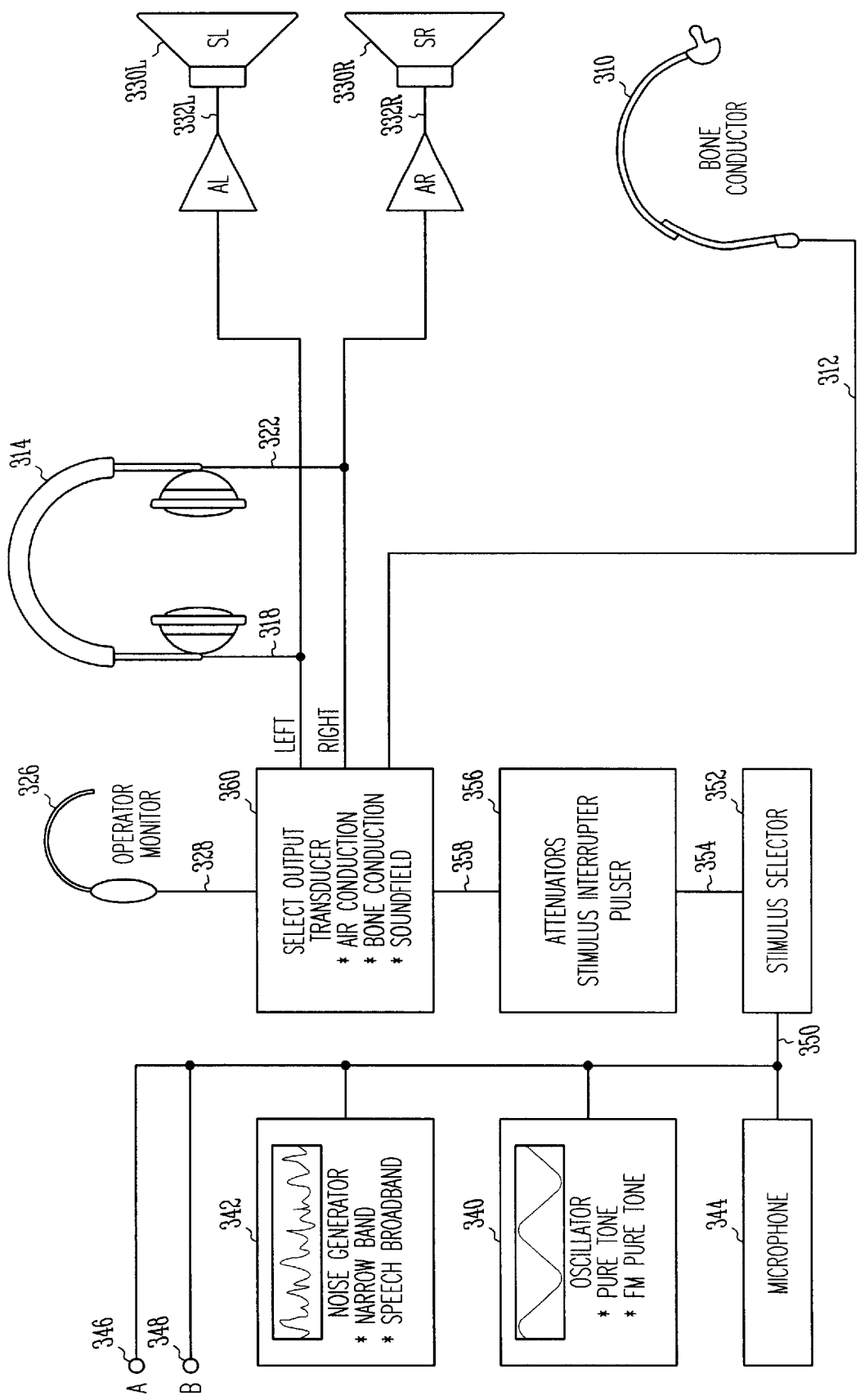
FIG. 9 is a functional block diagram illustrating selective control and functional performance of an audiometer that functions as an audiometer.

FIG. 9 is a functional block diagram illustrating selective control and functional performance of an audiometer that functions as an audiometer. An audiometer presents a variety of stimuli under strict frequency, temporal and level control to persons for the purpose of testing their hearing capability. Specifications for controlling these parameters are provided in ANSI Standard S3.6. In general, the audiometer includes three major sections, namely, a signal generation and selection portion; a signal shaping and control portion, including controlled signal attenuation, signal interruption, and signal pulsing; and a transducer selection portion.

Considering first the signal generation and selection functions, a controlled oscillator section 340 is capable of generating pure tone waves and frequency modulated pure tone waves. In this embodiment, the oscillator system 340 generates selectable sign waves at up to 11 discrete octave and ½-octave audiometric test frequencies ranging from 125 Hz to about 8,000 Hz for obtaining the pure tone audiograms. The oscillator section 340 includes circuitry that can cause the sign waves to exhibit "warble tones". This warbling tone source is produced by frequency modulation and is used for the purpose of breaking up standing waves in the test room. Typical frequency modulation rates are about 5 Hz with a frequency deviation of about 10%.

A noise generator system 342 is used for masking a better ear while testing a poorer ear. The noise generator 342 generates a white noise initially which is filtered into speech-spectrum noise. The white noise signal is also filtered into narrow bands of noise centered at the 11 discrete octave and one-half octave audiometric test frequencies for use in soundfield testing. Narrow band noise is typically about one-third octave in bandwidth. Both types of noise are available to the hearing professional for different masking applications.

In addition to the oscillator section 340 and the noise generator section 342, live voice testing can be accomplished via microphone 344.

External inputs can be provided through external input A labeled 346 and external input B labeled 348. External signal sources (not shown) such as tape recorders, CD players and the like may be utilized. The various stimulus providers are coupled via line 350 to a stimulus selector section 352. This stimulus selector is under operator control and allows the operator to select from among the external signal sources, the oscillator section 340, the noise generator section 342, or the external microphone 344. The output of the selective stimulus source is provided on line 354 to the signal modifying section 356 which includes attenuator circuits, stimulus interrupter circuits, and pulsar circuits. The attenuator circuits provide a calibrated amount of attenuation of the stimulus signals so as to ascertain the amount of hearing loss a person has. Normally five dB steps are provided for zero dB to 100 dB, depending on frequency. Differing ranges of steps may be achieved at a relatively higher cost of production.

A stimulus interrupter circuit turns the selected stimulus off and on under manual control with specific rise and fall times so as to not create spurious energy at frequencies other than the desired test frequency.

A pulser circuit works automatically to turn the stimulus signals off and on with specific rise and fall times. Again, the purpose is to control the stimulus pulser such as to not create spurious energy at frequencies other than the desired test frequency. A typical repetition rate would be on the order of about 0.5 second and duty cycle is typically 50%.

The shaped and controlled stimulus signals are provided on line 358 to an output transducer selection portion 360. It is the function of the output transducer selection portion to allow the operator to direct the selected output signals to the air conduction headphones 314, the bone conductor 310, or a loudspeaker system comprised, for example, of speakers 330L and 330R. As mentioned above, more speakers can be utilized as might be necessary. Each of the output transducer systems is utilized in a different diagnostic application in assessing the patient's hearing capability.

Figure 10:
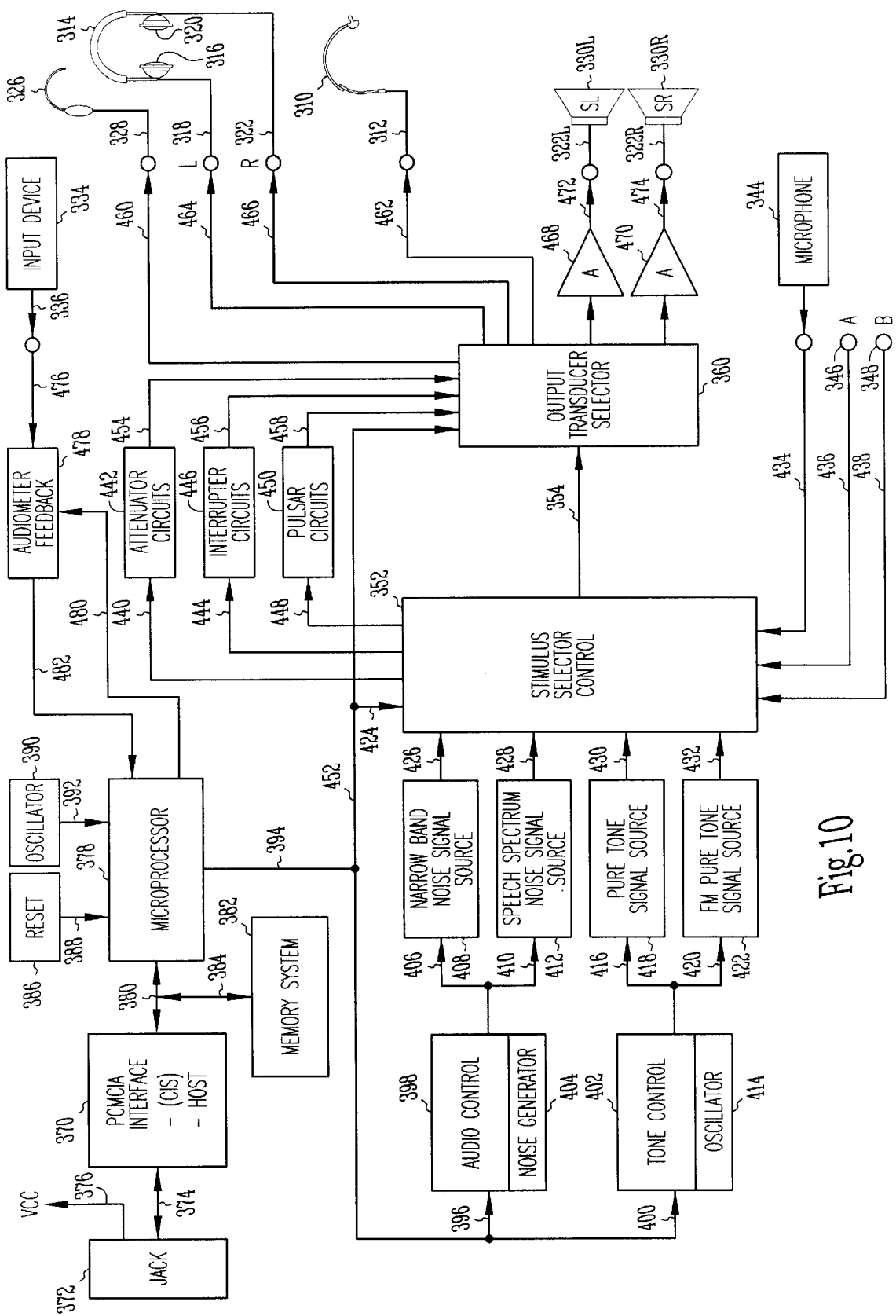
FIG. 10 is a block diagram of a PCMCIA audiometer Card.

FIG. 10 is a block diagram of a PCMCIA audiometer Card. It illustrates the circuit interaction to achieve the functionality described with respect to FIG. 9. The interrelationship of the host computer and the Card is similar to that described with respect to FIG. 6.

The PCMCIA audiometer Card has a PCMCIA interface 370 that is coupled to jack 372 via line 374, where lines 374 include circuits for providing power and ground connections from the host, and circuits for providing address signals, data signals, and control signals back and forth from the PCMCIA Card to the host. Line 376 provides VCC power to the Card. The PCMCIA interface 370 includes the Card Information Structure (CIS) that is utilized for providing signals to the host computer indicative of the nature of the Card and setting the configuration parameters. The CIS contains information and data specific to the Card, and the appropriate couples comprising components of information in the CIS. A microprocessor 378 includes a processor portion that receives signals from the PCMCIA interface 370 via lines 380 and provides signals to the interface over lines 380. An on-board memory system (not shown) is provided for storing bootstrap instructions that are utilized for initializing the microprocessor operation upon startup, and for storing information that may be downloaded from the host computer. A memory system 382 is coupled via line 384 to the microprocessor 378 and the interface 370. The memory system is utilized for storing software transmitted from the host and for storing data indicative of the sound parameters being administered.

A reset circuit 386 is coupled via line 388 to the microprocessor and is utilized for initializing the microprocessor.

An oscillator section 390 is coupled via line 392 to the microprocessor 378 and is utilized for providing timing functions to the circuits of the microprocessor.

Circuit component selection can be as described above with regard to FIG. 6.

The initialization and setup of the microprocessor 378 and the memory system 382 is accomplished upon insertion of the PCMCIA Card in the appropriate PCMCIA socket, in a manner similar to that described above.

Once inserted and initialized, microprocessor 378 provides control signals on line 394 that operates to provide selection signals on line 396 to control the operation of the audio control circuits 398, and on line 400 to control the functionality of the tone control circuits 402. The audio control section 398 includes noise generator circuits 404 that provide white noise output signals on line 406 to the narrow band noise signal source circuits 408 and on line 410 to the speech spectrum noise signal source 412. The frequency ranges are selectable by parameters provided by the microprocessor 378.

The tone control section 402 includes a controllable oscillator circuit 414 and functions to provide signals on line 416 to the pure tone signal source circuits 418, and on line 420 to the frequency modulated (FM) pure tone signal source 422. The tone control section 402 operates under control of the microprocessor 378 to generate the selected frequencies and modulations for the hearing test specified. This reflects selections made at the host computer and downloaded to the audiometer PCMCIA Card.

The stimulus selector control 352 is controlled by the microprocessor 378 providing control signals on line 424, and operates to select from among the various sources of stimulus available for the system. These sources of stimulus signals are from the narrow band noise signal source via line 426; from the speech spectrum noise signal source via line 428; from the pure tone signal source via line 430; from the FM pure tone signal source via line 432; from the external microphone 344 via line 434; from external source A via line 436; and from external source B via line 438.

The selected stimulus signals provided by the stimulus selector control 352 are selectively provided on line 440 to the attenuator circuits 442, on line 444 to the interruptor circuits 446, or on line 448 to the pulser circuits 450. The stimulus selector control circuits 352 provide control signals on line 354 to the output transducer selector circuits 360 forming a portion of the control of selection of the appropriate output transducers to be utilized during the testing process. Microprocessor 378 provides control signals on line 452 to form a part of the output transducer selection.

The stimulus signals are provided from the attenuator circuits 442 on line 454, from interrupter circuits 446 on line 456, and from pulser circuits 450 on line 458 to the output transducer selector circuits 360.

The output transducer selector circuits 360 operate to select from among the various shaped stimulus pulses available and to direct them to the appropriate output transducers. The output stimulus signals can be provided to a monitor 326 via line 460. If the bone conductor 310 is selected, output signals are provided on line 462 thereto. If the air conduction headphones 314 are selected, the signals to the left and right ears are provided on lines 464 and 466, respectively. When the soundfield speakers 330L and 330R are selected, the selected output signals are passed through amplifiers 468 and 470 to lines 472 and 474, respectively, for driving the speakers. To record various parameters resulting from the audiometer testing, a input device 334 can provide selected signals on line 476 to an audiometer feedback circuit 478. The audiometer feedback circuit 478 operates under control of the microprocessor 378 through control signals provided on line 480. The microprocessor 378 is programmed to cause the audiometer feedback 478 to provide signals on line 482 to the microprocessor. These feedback signals are either passed directly by the microprocessor 378 back to the host, or are stored temporarily in the memory system 382 for uploading to the host at various intervals in the hearing testing process.

It can be seen, then, that the audiometer PCMCIA Card functions under control of the host to provide selected ones of a number of available sound sources for testing different parameters of a patient's hearing response. The results of the hearing test can be fed back to the host either for use in forming displays at the host for allowing the hearing professional to select hearing aid programming parameters to be applied via the hearing aid programmer, or for interactively adjusting the hearing aid programming parameters automatically.

Figure 11:
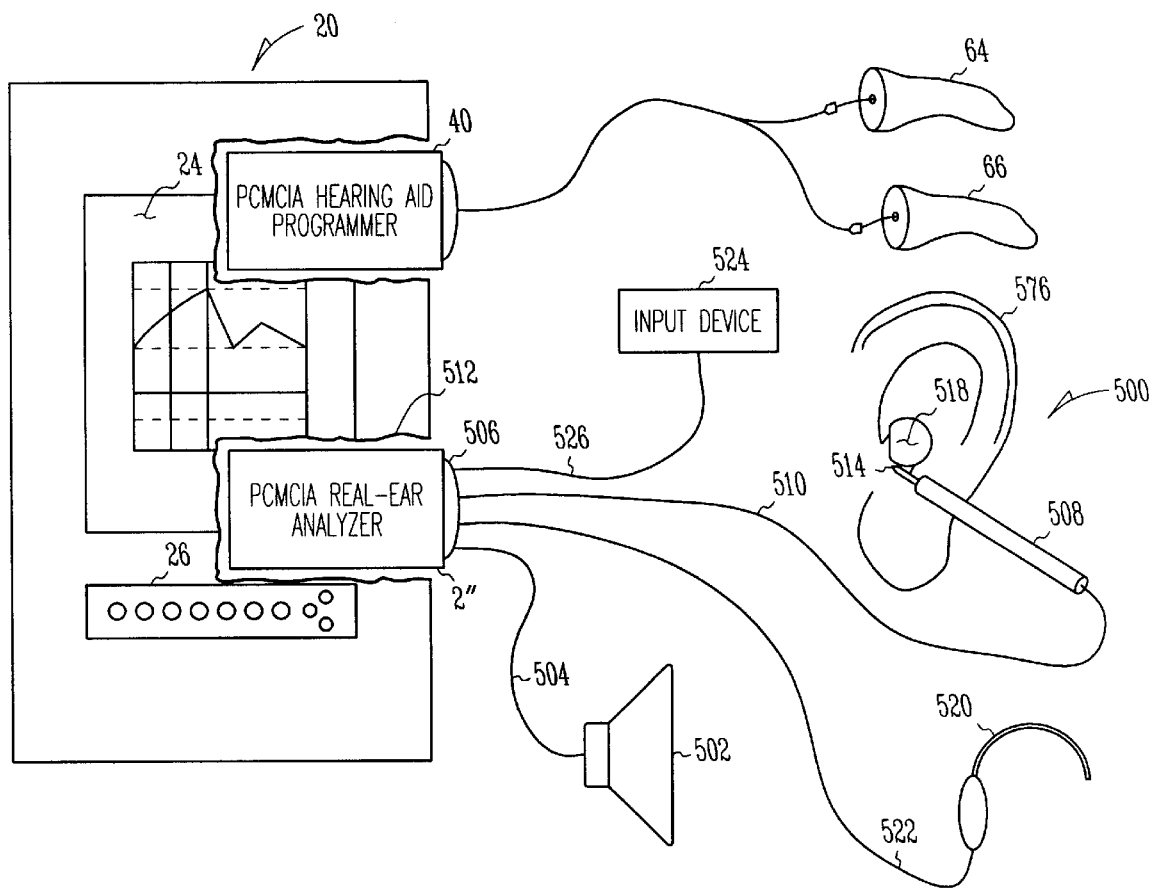
FIG. 11 is a block diagram illustrating the functional relationship of the host computer, the Card used to program hearing aids, and a real-ear Card used to analyze performance of a hearing aid in a patient's ear.

FIG. 11 is a function block diagram illustrating selective control and functional performance of a real-ear hearing-related analyzer. A PCMCIA real-ear analyzer system 500 is made up of a PCMCIA real-ear analyzer Card 2", an output speakers system 502 coupled via line 504 to jack 506, and a probe microphone 508 coupled via line 510 to jack 506. The PCMCIA real-ear analyzer Card 2" is shown within broken away portion 512 of host computer 20. A single speaker 502 is shown, but it is understood that multiple speakers may be utilized for positioning at various locations around the patient whose hearing is being analyzed.

As shown, the real ear system 500 has the probe microphone with a long tube 514 mounted at the distal end of probe microphone 508. As illustrated, the long tube 14 is positioned within the ear canal of ear 516. The probe microphone 508 is utilized to pick up the sound pressures produced in the ear canal of the patient in response to various sound conditions being administered to the patient. The testing of the patient can be accomplished without any aid to the hearing of the patient. This is identified as real-ear unaided response (REUR). Another testing process can be utilized in measuring the hearing response of the patient with the ear canal occluded. This is referred to as the real-ear occluded response (REOR). Yet another set of test parameters that can be taken is the real-ear saturation response, referred to as the RESR. A fourth test that can be accomplished is the real-ear insertion gain frequency response (REIR). Finally, the patient can be analyzed with a hearing aid in place, such as hearing aid 518, and is identified as the real-ear aided response (REAR).

The real-ear system records the output measured by the probe microphone 508 in the ear canal.

The system can be monitored by the hearing care professional through a monitor headset 520 that is coupled via line 522 to connector 506.

The real-ear system 500 can provide feedback directly to the PCMCIA real-ear analyzer via an input device 524 that provides feedback signals on line 526 to connector 506. The information thus fed back can either be provided to the host computer 20 for display on display 24, or can be used for modifying hearing aid programming parameters on an interactive basis. When the hearing aid parameters are automatically adjusted by host computer 20, the PCMCIA hearing aid programmer 40 can have its hearing aid programming signals appropriately modified such that hearing aids 64 and 66 can have their respective programming adjusted to reflect the results of the real-ear analysis.

Figure 12:
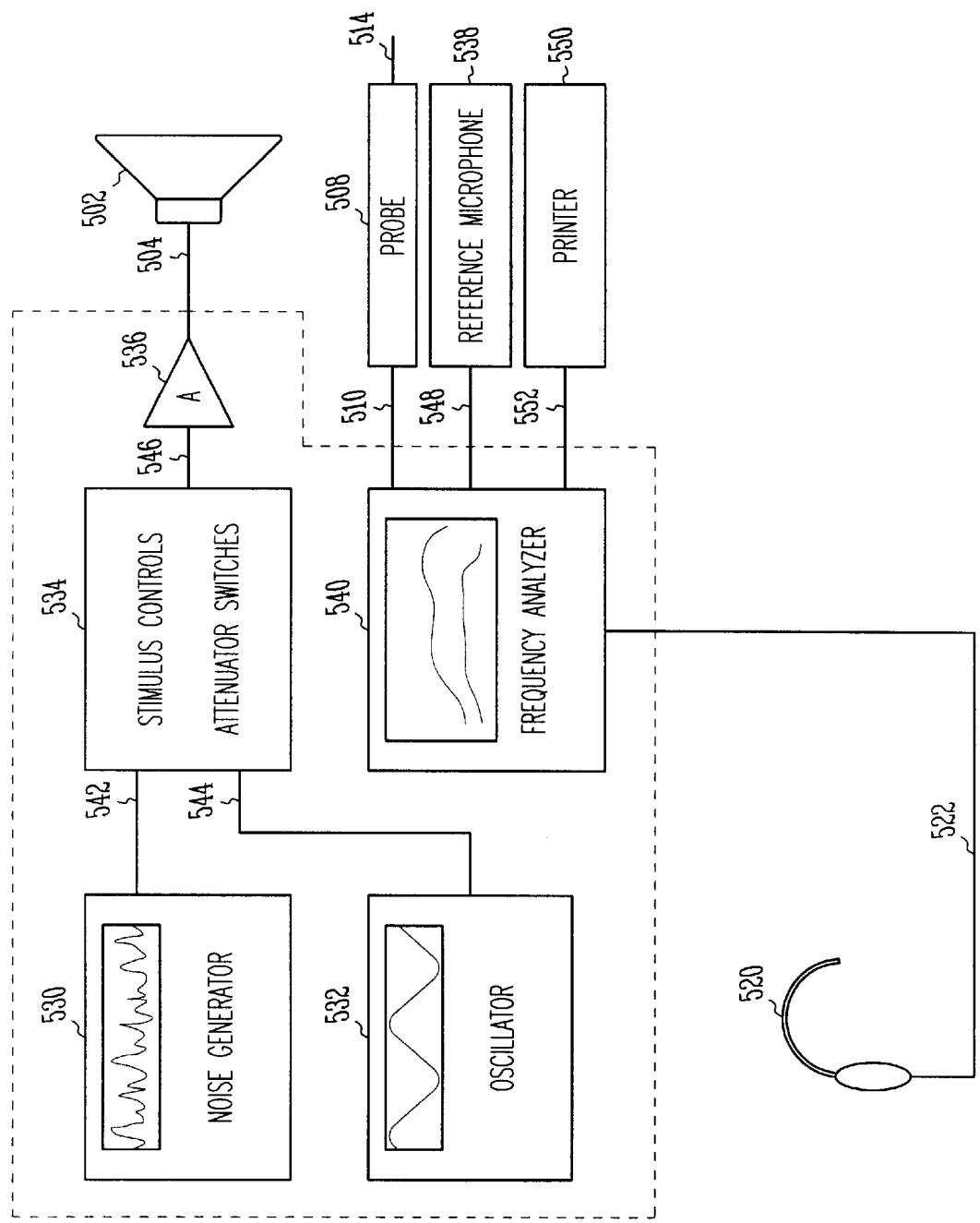
FIG. 12 is a functional block diagram illustrating selective control and functional performance of a real-ear hearing-related analyzer.

FIG. 12 is a functional block diagram illustrating selective control and functional performance of a real-ear hearing-related analyzer. A real-ear system records the sound levels occurring within the ear canal of a patient under various unaided, modified, or aided hearing conditions. With a hearing aid in place, the real-ear system records the output of the hearing aid in the wearer's ear canal utilizing the probe tube 514 of the probe microphone 508. The main components of a real-ear system are the stimulus generators comprising a noise generator 530 and an oscillator section 532, the stimulus controls 534, the output amplifier 536, the loudspeaker system 502, the probe microphone 508, a reference microphone 538, and a frequency analyzer system 540.

The noise generator section 530 provides narrow-band noise and speech spectrum (broad-band) pseudo-random or random noise signals. The narrow band noise signals is typically generated at about one-third octave in band width. The pseudo-random and random noise signals generally include a long-term speech spectral shape.

The controlled oscillator section 532 generates swept sign waves and narrow band noises produced over a frequency range of at least 200 Hz to 6,000 Hz.

The controlled stimulus signals are provided from the noise generator 530 on line 542, and from the controlled oscillator section 532 on line 544 to the stimulus control section 534.

The stimulus control section 534 selects the desired stimulus signals, the input level, and the frequency range, if applicable, desired by the health care professional. The stimulus control section 534 provides the selected input stimulus signal on line 546 to amplifier 536 for driving the speaker system 502.

The probe microphone 508 monitors the output signal level versus frequency that is produced in the wearer's ear canal, and when the test is for aided response, measures the output produced by the wearer's hearing aid.

The reference microphone 538 monitors the level of test stimulus at a reference location. Its purpose is to control the level of the spectrum of the input stimulus to desired shape. The shape of the input signal may be flat or is shaped to a long-term speech spectrum. The output of the referenced microphone 538 is provided on line 548 to the frequency analyzer 540.

The frequency analyzer 540 displays the output of the probe microphone 508 versus frequency and acoustic gained or acoustic output sound pressure levels (SPL). The frequency analyzer 540 can be either analog-based or digitally-based, and functions to display the output from the probe microphone 508 in comparison to a predicted or anticipated frequency response.

To create a record of the analysis, a printer 550 is driven by line 552.

Figure 13:
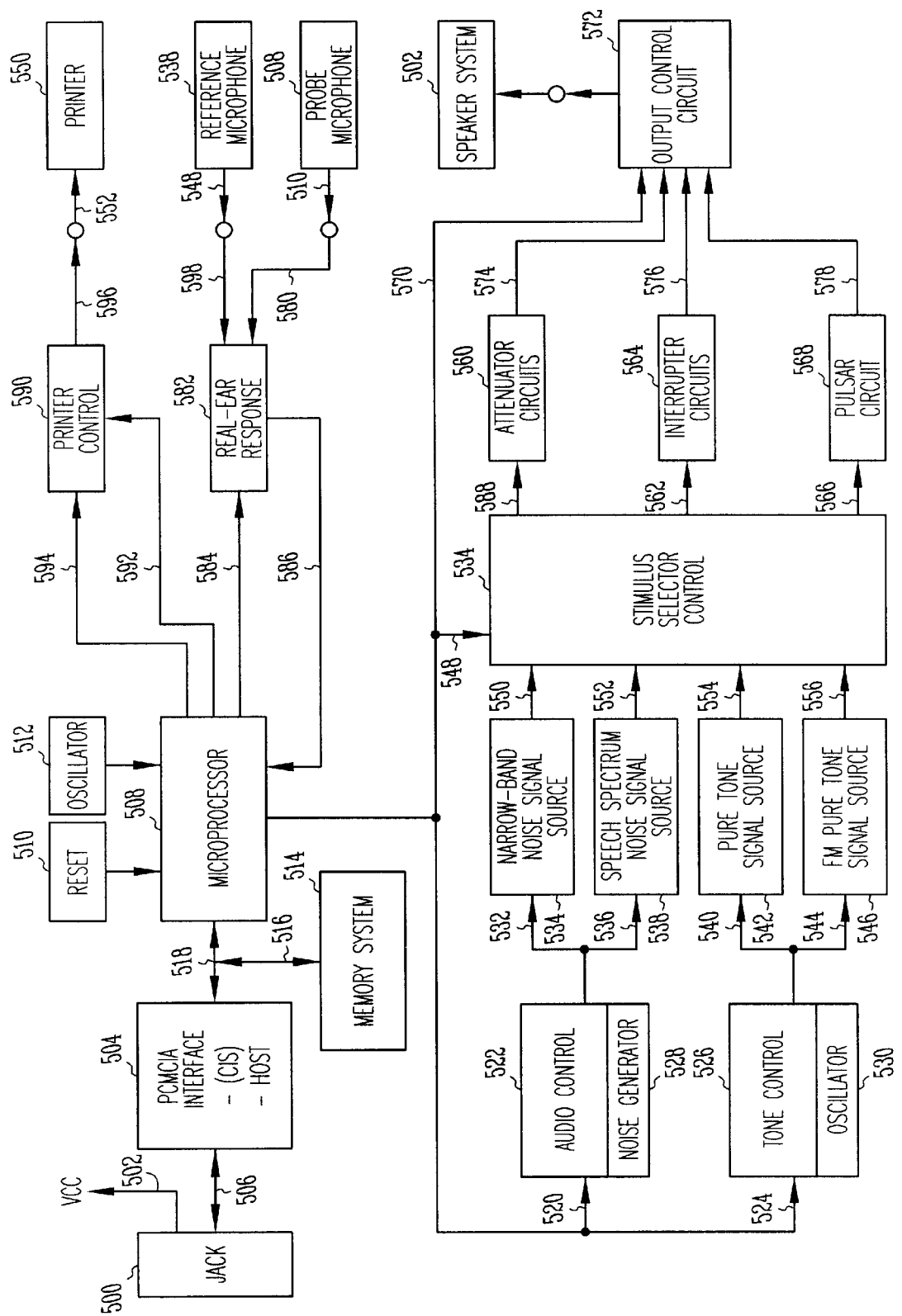
FIG. 13 is a block diagram of a PCMCIA real-ear Card.

FIG. 13 is a block diagram of PCMCIA real-ear Card. The real-ear Card has a jack 500 for plugging into a PCMCIA slot in a host computer, and provides VCC power on line 502 to the Card. A PCMCIA interface 504, with the CIS and the host interface, provide card identifying information to the host computer via line 506 and receive signals from the host computer via line 506. A microprocessor 508 is coupled to reset circuit 510 and to oscillator 512 as described above. A memory system 514 communicates via line 516 with the interconnection 518 between interface 504 and microprocessor 508.

The microprocesor 508 controls the functioning of the real-ear analyzer system and provides control signals on line 520 to the audio control section 522, and on line 524 to the tone control section 526. The audio control section 522 includes noise generator circuits 528, and the tone control section 526 includes controlled oscillator circuits 530.

The audio control section generates signals on line 532 for controlling the narrow-band noise signal source 534 and, on line 536 to control the speech spectrum noise signal source.

The tone control section 526 provides the swept sign waves on line 540 to the pure tone signal source 542 and on line 544 to the FM pure tone signal source 546.

The stimulus control section 534 is controlled by microprocessor 508 with signals received on line 548, to select the appropriate input signals. The input signals are provided on line 550 from the narrow-band signal source 534, on line 552 from the speech spectrum noise signal source 538, on line 554 from the pure tone signal source 542, and on line 556 from the FM pure tone signal source 546. The stimulus selector control 534 selectively provides output signals on line 558 to the attenuator circuits 560, on line 562 to the interruptor circuits 564, or on line 566 to the pulser circuit 568.

The microprocessor 508 provides control signals on line 570 to the output control circuits 572 for appropriately selecting the stimulus signal to be applied to speaker system 502. Attenuator circuits 560 provide signals on line 574, interrupter circuits 564 provide signals on line 576, and pulser circuit 568 provides signals on line 578 to the output control circuit 572.

In response to the various selectable stimulus signals, probe microphone 508 provides sensed real-ear response signals on line 510. These signals are provided on line 580 to the real-ear response circuits 582. The real-ear response circuits 582 operate under control of control signals provided on line 584 from the microprocessor 508, to feed back selected signals via line 586 to the microprocessor. The microprocessor 508 either directly transmits the real-ear response parameters through the interface 504 to the host computer, or temporarily stores the responses in the memory system 514 for later uploading to the host computer.

The frequency analysis shown in FIG. 12 as frequency analyzer 540 is accomplished in the host computer (not shown in FIG. 13) where the response parameters are displayed on the host computer's display in correlation to predicted or reference wave shapes. In this manner, the real-ear system can assess the efficacy of aided hearing response and can interactively adjust hearing aid programming parameters to be applied by the host computer through the hearing aid programmer PCMCIA Card 40.

A printer control section 590 receives control signals from microprocessor 508 on line 592, and receives real-ear response data signals on line 594. The parameters to be recorded are provided on line 596, and thence to line 552 for printing by printer 550.

The reference microphone 538 provides reference signals on line 598 to the real-ear response circuits 582 for use in the analysis of the real-ear response from the probe microphone 508.

Figure 14:
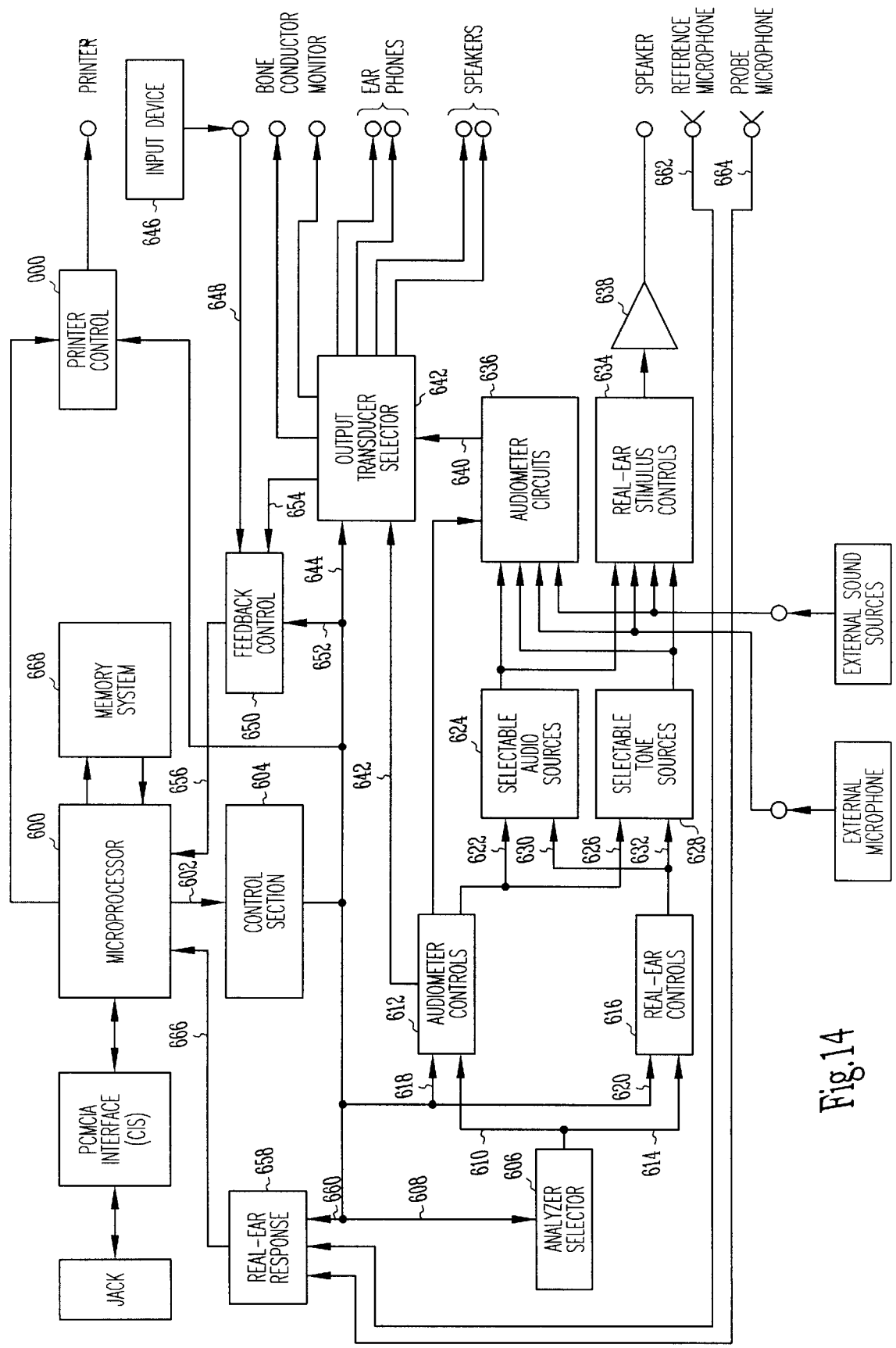
FIG. 14 is a block diagram of PCMCIA Card including a hearing-related analyzer having selectable audiometer and real-ear functions.

FIG. 14 is a block diagram of a PCMCIA Card including a hearing-related analyzer having selective audiometer and real-ear functions. In this configuration, the individual functions of the audiometer PCMCIA Card described in FIG. 10 and the functionality of the real-ear analyzer described with regard to FIG. 13 are combined on a single PCMCIA Card. In this configuration, a microprocessor 600 provides control signals on line 602 to a control section 604 that functions to selectively drive the analyzer selector 606 via control lines 608. The analyzer selector provides control signals on line 610 to the audiometer controls 612 and on line 614 to the real-ear controls 616. The control section 604 provides control signals on lines 618 and 620 to the audiometer control 612 and the real-ear control 616 respectively. The audiometer controls 612 provide control signals on line 622 to the selectable audio sources 624 and on line 626 to the selectable tone sources 628. The real-ear control 616 provides control signals on line 630 to the selectable audio sources 624 and on line 632 to the selectable tone sources 628. These controls function to select the appropriate controlled oscillator tone sources and noise generator signal sources as described above. The selectable tone sources are applied to the real-ear stimulus controls 634 and the audiometer circuits 636 respectively. Similarly, the selectable audio sources signals are provided to the audiometer circuits 636 and the real-ear stimulus control 634.

The real-ear stimulus control 634 drives amplifier system 638 and can drive one or more speakers as described above.

The audiometer circuit 636 provides signals on line 640 to the output transducer selector 642. The audiometer controls circuit 612 provide control signals on line 642 and the control section 604 provides control signals on line 644 to control the application of the selected stimulus signals to the various output terminals, as described above. An input device 646 is available to provide feedback signals on line 648 to the feedback control section 650. This feedback control section 650 operates under control of control signals received on line 652, the output from the output transducer selector 644 provided on line 654, and the input device input provided on line 648 to provide feedback data on line 656 to the microprocessor 600. The feedback signals can be indicative of various control parameters entered at the input device 646 and available to transmit to the host computer for use interactively in adjusting the programming parameters to be applied to the hearing aids to be programmed.

A real-ear response section 658 receives control signals on line 660 from control section 604, and input signals from a reference microphone on line 662, and from the probe microphone on line 664. The real ear response circuit 658 provides selected output signals on line 666 to the microprocessor 600 for transmission to the host computer either directly, or after temporary storage in the memory system 668, all as described above.

From the foregoing considerations, then, it can be seen that a unique PCMCIA Card for an audiometer can be provided for an audiometer system, as described with regard to FIG. 10, to provide a real-ear response and hearing analysis as described with respect to FIG. 13, or the interactive combined audiometer combining both the audiometer hearing analysis capability and the real-ear hearing response analysis.

Figure 15:
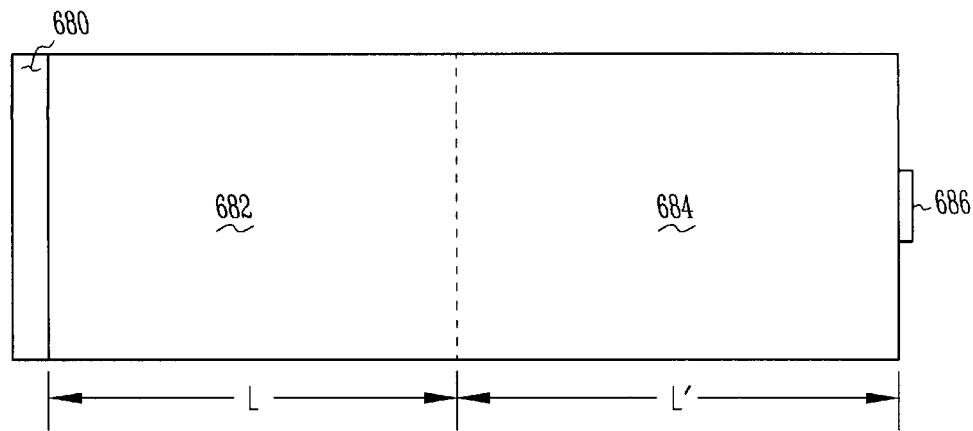
FIG. 15 is a block diagram of a portable hearing-related analyzer PCMCIA Card.

FIG. 15 is a block diagram of an expanded portable hearing-related analyzer PCMCIA Card. As described above, a basic PCMCIA Card has a PCMCIA jack portion 680 and a length L that approximates the depth of the PCMCIA slot. For those PCMCIA Cards that require additional area to mount components, an additional length L' can be provided. The additional length L' can be of the same width as the basic PCMCIA Card Types, can be lesser in width, or can be greater in width, since this dimension of the PCMCIA Card would be outside the body of the host computer. As illustrated, the basic portion 682 of the PCMCIA Card is physically extended into a second portion 684 for the expansion. Connector 686 is utilized to connect to the various input/output systems.

Figure 16:
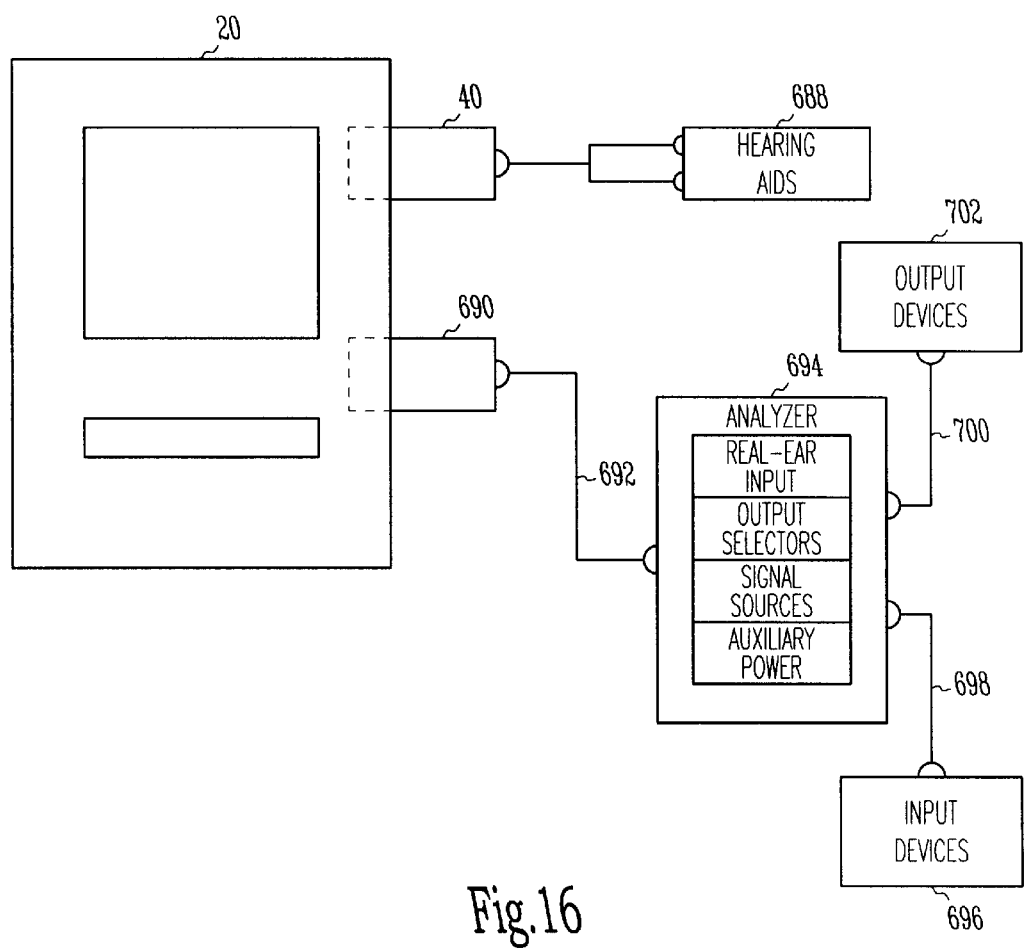
FIG. 16 is a block diagram of a portable hearing aid analyzer cable-connected to an associated PCMCIA interface Card.

FIG. 16 is a block diagram of a portable hearing-related analyzer cable connected to an associated PCMCIA interface Card. In this configuration, the host computer 20 has the PCMCIA hearing aid programming Card 40 coupled to the hearing aids 688 to be programmed. The hearing-related analyzer PCMCIA Card 690 is shown with a cable connection 692 to a hearing-related analyzer 694. In this configuration, the circuitry included on the audiometer PCMCIA Card 690 would include the PCMCIA interface, microprocessor, and memory system (not shown) described above. For those situations where the hearing-related analyzer 694 would require more structural capacity than could be provided on an expanded PCMCIA Card, for example, as shown in FIG. 15, a freestanding portable device could be assembled to provide the functionality described with regard to FIG. 10, FIG. 13 and FIG. 14. With a cable connected hearing-related analyzer 694 as shown, input devices 696 would provide signals via cable 698 to the audiometer. The hearing-related analyzer 694 would provide signals on cable 700 to the selected output devices 702, substantially as described above.

From the foregoing, it can be seen that the various stated purposes and objectives of the invention have been satisfied. A highly portable hearing-related analyzer system coupled to a host computer through the PCMCIA ports of the host processor have been described. It is, of course, understood that various modifications, additions, or deletions can be made without departing from the scope and intent of the invention. Further, various selections of components can be utilized to implement the various features of the invention.

It will be understood that this disclosure, in many respects, is only illustrative. Changes can be made in details, particularly in matters of shape, size, material and arrangement of parts without exceeding the scope of the invention. Accordingly, the scope of the invention is as defined in the language of the appended Claims.

What is claimed is:

1. A portable hearing analyzer and hearing aid programming system, comprising:
   a host including a processor and a memory operably connected to the processor;
   a card operably coupled to the processor, the card having circuitry configured to wirelessly connect to a hearing aid for programming the hearing aid; and
   a hearing analyzer operably coupled to the processor to generate selected hearing test signals and to transmit hearing test results to the host.

2. The system of claim 1, wherein the card having circuitry configured to wirelessly connect to a hearing aid is configured to connect to a hearing aid by an infrared transmission system.

3. The system of claim 1, wherein the card having circuitry configured to wirelessly connect to a hearing aid is configured to connect to a hearing aid by a radio frequency transmission system.

4. The system of claim 1, wherein the card is removably coupled to the host.

5. The system of claim 1, wherein the card includes a control processor and a memory system.

6. The system of claim 1, wherein the hearing analyzer includes a hearing analyzer card removably coupled to the host.

7. The system of claim 6, wherein the hearing analyzer includes a hearing analyzer circuit separate from the hearing analyzer card, and wherein the hearing analyzer circuit is in communication with the processor through the hearing analyzer card.

8. The system of claim 7, wherein the hearing analyzer includes a cable connection connecting the hearing analyzer card to the hearing analyzer circuit.

9. The system of claim 6, wherein the hearing analyzer includes a hearing analyzer circuit within the hearing analyzer card.

10. The system of claim 6, wherein the hearing analyzer card includes a processor system that produces hearing-related analyzing instructions; and wherein the hearing analyzer includes:
    a plurality of selectable audio signal sources;
    a first circuit coupled to the plurality of selectable audio signal sources and coupled to the processor system of the hearing analyzer card to select one of the plurality of selectable audio signal sources in response to predetermined ones of the hearing-related analyzing instructions.

11. The system of claim 10, wherein the hearing analyzer includes an audio signal device coupled to the first circuit to apply the selected audio signals to a person whose hearing is to be tested.

12. A system of claim 11, wherein the hearing analyzer includes:
    a feedback circuit having an input section to receive feedback signals and an output section; and
    a feedback control circuit coupled to the output section and coupled to processor system of the hearing analyzer to control transmission of the feedback signals to the host processor.

13. The system of claim 12, and further including in combination:
    a feedback device coupled to the input section, the feedback device including selection devices operable to feedback hearing analysis signals indicative of hearing responses resulting from the selected ones of the selected audio signals.

14. The system of claim 6, wherein the hearing analyzer card is a PCMCIA card.

15. The system of claim 14, wherein the card having circuitry configured to wirelessly connect to a hearing aid is a PCMCIA card.

16. The system of claim 1, wherein the card having circuitry configured to wirelessly connect to a hearing aid is a PCMCIA card.

* * * * *

UNITED STATES PATENT AND TRADEMARK OFFICE
CERTIFICATE OF CORRECTION

PATENT NO. : 6,647,345 B2
DATED : November 11, 2003
INVENTOR(S) : Bye et al.

It is certified that error appears in the above-identified patent and that said Letters Patent is hereby corrected as shown below:

Title page,
Item [56], References Cited, U.S. PATENT DOCUMENTS, delete "4,706,778" and insert -- 4,760,778 --, therefor.
FOREIGN PATENT DOCUMENTS, insert -- H04R -- after "5/2001".

Signed and Sealed this

Twenty-ninth Day of June, 2004

JON W. DUDAS
*Acting Director of the United States Patent and Trademark Office*